(12) United States Patent
Matsuura et al.

(10) Patent No.: US 10,188,406 B2
(45) Date of Patent: Jan. 29, 2019

(54) DRILL DEPTH MEASURING DEVICES AND METHODS

(71) Applicants: David G. Matsuura, Del Mar, CA (US); Robert I. Gelb, Solana Beach, CA (US); Philip J. Simpson, Escondido, CA (US)

(72) Inventors: David G. Matsuura, Del Mar, CA (US); Robert I. Gelb, Solana Beach, CA (US); Philip J. Simpson, Escondido, CA (US)

( * ) Notice: Subject to any disclaimer, the term of this patent is extended or adjusted under 35 U.S.C. 154(b) by 116 days.

(21) Appl. No.: 15/514,400

(22) PCT Filed: Sep. 25, 2015

(86) PCT No.: PCT/US2015/052243
§ 371 (c)(1),
(2) Date: Mar. 24, 2017

(87) PCT Pub. No.: WO2016/049467
PCT Pub. Date: Mar. 31, 2016

(65) Prior Publication Data
US 2017/0296204 A1    Oct. 19, 2017

Related U.S. Application Data

(60) Provisional application No. 62/055,520, filed on Sep. 25, 2014.

(51) Int. Cl.
*A61B 17/17* (2006.01)
*A61B 17/00* (2006.01)
*A61B 90/00* (2016.01)

(52) U.S. Cl.
CPC .............. *A61B 17/17* (2013.01); *A61B 17/00* (2013.01); *A61B 17/1707* (2013.01);
(Continued)

(58) Field of Classification Search
CPC ... A61B 17/17; A61B 2090/062; A61B 17/00; A61B 90/06
See application file for complete search history.

(56) References Cited

U.S. PATENT DOCUMENTS 4,329,985 A * 5/1982 Bonchek ................ A61B 17/00
604/185
4,399,813 A * 8/1983 Barber ............... A61B 17/1615
606/100

(Continued)

FOREIGN PATENT DOCUMENTS

WO    WO-02/17794 A1    3/2002
WO    WO-2006/074321 A2    7/2006
WO    WO-2012/125546 A1    9/2012

*Primary Examiner* — Christian Sevilla
(74) *Attorney, Agent, or Firm* — Mintz Levin Cohn Ferris Glovsky and Popeo, P.C.

(57) ABSTRACT

Described herein include embodiments of devices, systems and methods for measuring drill depth, such as drill depths in bone material. For example, embodiments of drill depth measuring systems and associated methods are described. Some drill depth measuring systems can utilize at least resistance, capacitance, optical and/or acoustic sensing features for assisting the drill depth measuring system with determining drill depths and types of tissue being drilled into. Various other related features, devices and methods are also described.

10 Claims, 22 Drawing Sheets

(52) U.S. Cl.
CPC ....... *A61B 90/06* (2016.02); *A61B 2017/0011* (2013.01); *A61B 2017/00026* (2013.01); *A61B 2017/00039* (2013.01); *A61B 2017/00057* (2013.01); *A61B 2017/00119* (2013.01); *A61B 2090/062* (2016.02)

(56) References Cited

U.S. PATENT DOCUMENTS

| | | | | |
|---|---|---|---|---|
| 4,710,075 | A | * | 12/1987 | Davison ................ A61B 17/16 33/512 |
| 4,815,467 | A | * | 3/1989 | Chestnut ................ A61B 90/39 606/185 |
| 5,133,720 | A | * | 7/1992 | Greenberg ............. A61B 17/02 606/86 R |
| 6,665,948 | B1 | | 12/2003 | Kozin et al. |
| 2005/0119663 | A1 | * | 6/2005 | Keyer ................ A61B 17/1622 606/96 |
| 2005/0240193 | A1 | | 10/2005 | Layne et al. |
| 2006/0241628 | A1 | | 10/2006 | Parak |
| 2009/0245956 | A1 | | 10/2009 | Apkarian et al. |
| 2009/0275950 | A1 | * | 11/2009 | Sterrett ............. A61B 17/1617 606/84 |
| 2010/0241129 | A1 | | 9/2010 | Markey et al. |
| 2011/0245833 | A1 | | 10/2011 | Anderson |
| 2013/0085505 | A1 | | 4/2013 | Markey et al. |

\* cited by examiner

DRILL DEPTH MEASURING DEVICES AND METHODS

CROSS-REFERENCE TO RELATED APPLICATION

The current application is a national stage entry, filed under 35 U.S.C. § 371, of International Application No. PCT/US2015/052243, filed on Sep. 25, 2015, and claims priority to U.S. Provisional Patent Application Ser. No. 62/055,520, filed on Sep. 25, 2014 and entitled "Drill Depth Measuring Devices and Methods," which are incorporated by reference herein in their entireties.

TECHNICAL FIELD

The subject matter described herein relates to devices, systems and methods for measuring and determining various characteristics related to drilling into tissue, such drill depth and tissue type being drilled into.

BACKGROUND

Some surgical procedures involve the drilling a hole in various tissue, such as bone. However, determining drill depth into such tissue during a surgical procedure can be difficult. This can result in errors associated with the drilled holes, such as the holes being too deep or not deep enough. In addition, determining drill depth can be time consuming due to, for example, the surgeon having to remove or back the drill out from the hole in order to determine the depth of the hole formed by the drill. If the hole depth is not of sufficient depth, the surgeon may have to re-insert the drill into the hole and continue drilling until a satisfactory hole depth is formed in the bone. Hole depths that are made too deep can result in complications and can require additional drill holes to be made. This can result in prolonged surgical procedures, as well as increased costs and recovery times for patients.

SUMMARY

Aspects of the current subject matter can include devices, systems and methods for measuring and determining various characteristics related to drilling into tissue, such drill depth and tissue type being drilled into. For example, various implementations of a drill depth measuring system including a drill guide device are described, which can detect types or changes in tissue being drilled into, as well as drill depth into tissue, such as bone and soft tissue.

In one aspect, a drill guide device or smart drill guide is described that can include a sensing circuit configured to sense a change in at least one of a resistance and a capacitance of a tissue having a drill bit forming a hole in the tissue. In addition, the drill guide device can include a processor configured to determine, based on the sensed change, at least one of a type of tissue the drill bit is forming the hole in and a depth of the hole. Additionally, the drill guide device can include a display for displaying information relating to the at least one of the type of tissue and the depth of the hole determined by the processor.

In some variations one or more of the following features can optionally be included in any feasible combination. The drill guide feature can have an elongated hollow shaft that assists with controlling a location and an angle of the drill bit relative to the tissue. The drill guide device can include a measuring feature in communication with the processor, the measuring feature can provide the processor with data that allows the processor to determine the depth of the hole. The measuring feature can include a Hall Effect sensor coupled to the drill guide device and a magnet providing a magnetic field that is coupled to the drill bit, and the Hall Effect sensor can sense data characterizing the magnetic field. The measuring feature can include an optical device that detects data associated with one or more markings positioned along a sleeve coupled to the drill bit or along the drill bit, with each of the one or more markings corresponding to the depth of the hole. The measuring feature can include a lever pivotally coupled at a proximal end to the drill guide device and a distal end of the lever being forced against a part of a drill that is coupled to the drill bit, and wherein movement of the drill causes a pivot of the lever, the pivot can be sensed by a sensor that communicates the sensed pivot to the processor for determining the depth of the hole. The measuring feature can include a location sensor and a spring extending between a drill coupled to the drill bit and a drill guide feature of the drill guide device, the spring can include at least one location indicator along the length of the spring, and the location sensor can detect a position for each of the at least one location indicator, with each detected position being communicated to the processor for determining the depth of the hole. The measuring feature can include a camera that collects images for processing by the processor having an image processing software that determines, from the captured images, the depth of the hole. The measuring feature can include a light emitting device and a reflective surface of a drill coupled to the drill bit, with the light emitting device sensing data characterizing a reflection of light emitted from the light emitting device and reflected off of the reflective surface. The measuring feature can include an optical sensor or camera for detecting a vertical position of a flute of the drill bit relative to the tissue. The measuring feature can include a microphone that collects audio data defining at least one of a volume, a frequency and an amplitude of during drilling of the drill bit into the tissue. The measuring feature can include a piezo element.

The drill guide device can include an alarm that provides at least one of an audio alarm and a visual alarm based on the type of tissue the drill bit is forming the hole in or the depth of the hole. The drill guide device can include a drill coupled to the drill bit, the drill configured to assist the drill bit with forming the hole in the tissue. The display can be a user interface that accepts user input for sending to the processor. The display can be located along a body of the drill guide device and is viewable by a user. The sensing circuit can include at least one of a Wheatstone bridge, a capacitance circuit, and a resistance circuit.

In another interrelated aspect of the current subject matter, a method includes sensing, with a sensing circuit of a drill guide device, at least one of a capacitance and a resistance of a tissue having a drill bit forming a hole in the tissue. In addition, the method can include determining, with a processor associated with the drill guide device and based on the sensed at least one of the capacitance and the resistance of the tissue, one or more of a type of tissue being drilled into with the drill bit and a depth of a drilled hole in the tissue. Additionally, the method can include displaying, on a display associated with the drill guide device, the determined one or more of the type of tissue being drilled into and the depth of the drilled hole.

In some implementations, the method can further include providing at least one of an audio alarm and a visual alarm based on the determined one or more of the type of tissue being drilled into and the depth of the drilled hole. In addition, the method can further include sensing, from a sensor associated with the drill guide device, data associated with a movement of the drill bit during drilling of the drilled hole. Additionally, the method can further include determining, based on the sensed data, a depth of the drilled hole. The sensor can include one or more of a Hall Effect sensor, an optical sensor, a camera, and a microphone.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
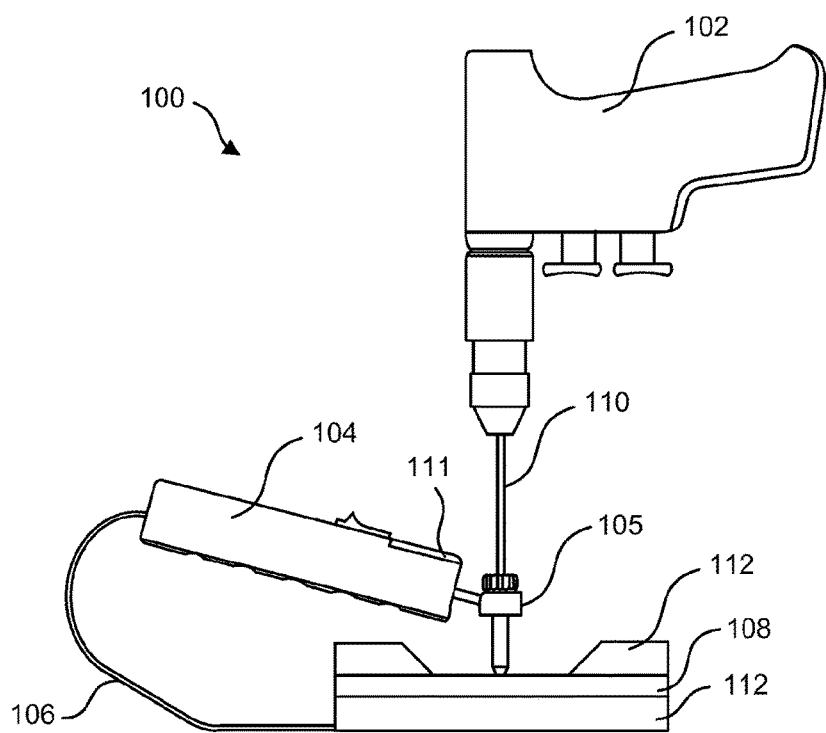
FIG. 1 shows a side view of an embodiment of a drill depth measuring system.

Some surgical procedures involve drilling a hole in various tissue, such as bone. When drilling such holes, a certain depth of the hole can be desired or required. However, achieving the desired or required drill depth can be difficult to determine and achieve. Complications associated with the surgical procedure can also be encountered when creating or drilling the hole, such as if the hole is made too deep. Described herein include various embodiments of a drill depth measuring system that can assist with monitoring and controlling the drill depth into tissue, such as bone. As such, the drill depth measuring system can assist with preventing complications associated with drilling into tissue during surgical procedures, as well as saving time and money by making such drilling more precise and efficient. In addition, the drill depth measuring system can provide a user with a drill depth measurement, which can allow the user to then select an appropriate screw length for inserting into the drilled hole.

In some implementations, the drill depth measuring system includes a smart drill guide that can be used with a drill device. The drill device can couple a drill bit that can be used for drilling into tissue, such as bone. The drill device and drill bit can be specialized for surgical use, such as sterilizable and/or disposable. However, any variety of drill devices and drill bits can be used, including those that are commercially available.

The smart drill guide can include a drill guide feature that assists with guiding the drill bit into tissue, such as at a desired angle relative to the surface of the tissue (e.g., at a substantially 90 degree angle). The drill guide feature can be secured into a position relative to the tissue prior to commencing drilling into bone, thereby controlling the location and angle of drilling. The smart drill guide can also assist with monitoring and controlling the drill depth into tissue, as will be explained in detail below. As such, the smart drill guide can assist with one or more of a location, angle, and depth of a hole created in tissue, such as bone.

In some implementations, the smart drill guide can include a sensing circuit that can assist with determining a resistance and/or capacitance in the tissue that the drill bit is advancing into. For example, the drill depth measuring system can include a ground wire that extends and provides a conductive path between the sensing circuit and the tissue. In addition, the sensing circuit can be in communication with the drill guide feature and drill bit, thereby creating a conductive path through the tissue. As the drill bit is advanced through the tissue, the conductance and/or resistance detected by the sensing circuit can change, which can be processed by a processor associated with the smart drill guide for determining one or more characteristics associated with the drilled hole.

For example, a change in resistance and/or capacitance sensed by the sensing circuit can indicate a change in tissue type being drilled into or approaching. In some implementations, a processor can determine (e.g., via an algorithm) what type of tissue is being drilled into and/or approaching based on such conductance and/or resistance sensed by the sensing circuit. In addition, a drill depth can be determined by the processor (e.g., via an algorithm), such as from data collected from a sensor and/or measuring feature. The information collected and/or determined by the sensing circuit and/or processor can be communicated to a user, such as by providing such information on a display or via an alarm associated with the smart drill guide. This can allow a user to monitor drilling into tissue, including in real-time, and precisely control drill depth into the tissue.

In some implementations, the drill depth measuring system can include one or more measuring features for determining drill depth. For example, the smart drill guide can include one or more sensors (e.g., Hall Effect sensor, optical sensor, acoustic sensor, etc.) that can detect a distance traveled by the drill bit, such as relative to the drill guide feature. This information can be used to determine a measured distance that the drill bit has traveled into the tissue (i.e., how deep the drilled hole is). As such, some implementations of the drill depth measuring system can include more than one ways to monitor and measure drill depth, including any of the features and configurations described herein.

Figure 2:
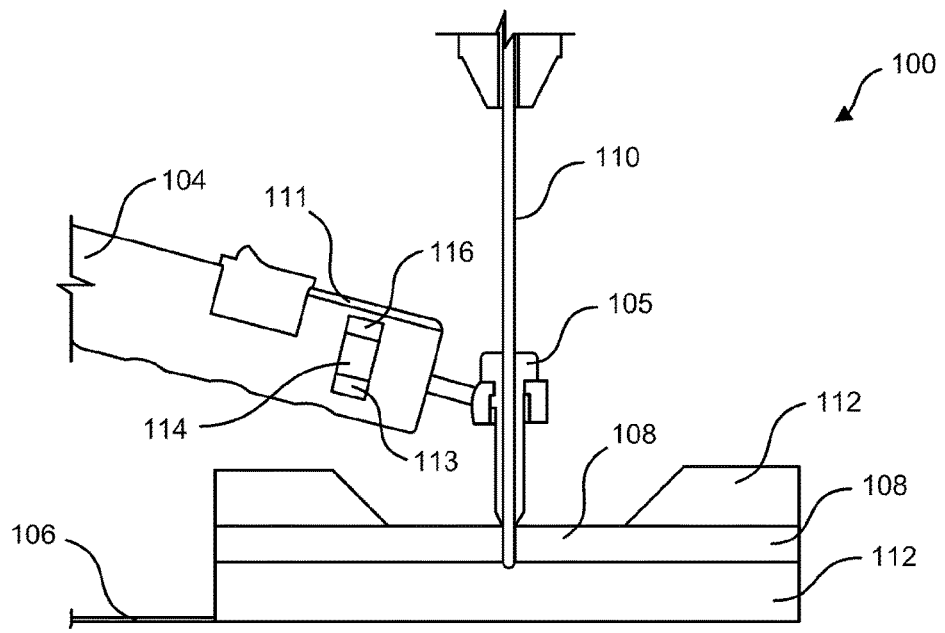
FIG. 2 shows a cross section side view of a drill bit of the drill depth measuring system of FIG. 1.

FIGS. 1 and 2 illustrate an embodiment of a drill depth measuring system 100 that includes a drill 102, a smart drill guide 104, and a ground wire 106. As shown in FIG. 2, a drill bit 110 extending from the drill 102 can form a hole in tissue, such as bone 108 and/or soft tissue 112. A drill guide feature 105 of the smart drill guide 104 can assist in positioning and angling the drill bit 110 into the tissue.

The ground wire 106 can provide a conductive pathway between a sensing circuit 114 of the smart drill guide 104 and a tissue (e.g., bone 108, soft tissue 112, etc.) being drilled into. The drill guide feature 105 and drill bit 110 can also provide a conductive pathway between the sensing circuit 114 and the tissue. The sensing circuit 114 can assist in sensing a resistance and/or capacitance of the tissue that the drill bit 110 is drilling into.

In addition, when the drill bit 110 meets a tissue interface (e.g., bone 108 to soft tissue 112), an electric change (e.g., change in resistance, voltage) can be sensed by the sensing circuit 114. This can be due to a change in material composition between the interfacing tissues, which can have different conductive properties. In addition, the smart drill guide 104 can include a processor 116 that is in communication with the sensing circuit 114 such that it can process the sensed electric changes and thereby determine (e.g., via an algorithm) a drill depth into the tissue and/or a change in tissue type that the drill bit 110 is drilling into. As such, the depth of the drill bit 110 into the tissue can be monitored, including measured and recorded by the smart drill guide 104 in real time. The smart drill guide 104 can also provide information relating to the position of the drill bit 110 and/or surrounding tissue when the drill bit 110 is not moving, such as in a resting position within the bone 108, as well as when the drill bit 110 is advancing into and/or being retracted from a hole formed in the tissue.

The drill guide feature 105 can include an elongated hollow shaft with an interior passageway that is large enough to allow the drill bit 110 to pass through, but also prevent the drill bit 110 from becoming misaligned. The drill guide feature 105 can provide a conductive pathway between the sensing circuit 114 and the drill bit 110, which can allow the sensing circuit 114 to monitor changes in resistance and/or capacitance in the tissue that the drill bit 110 is drilling into.

Some implementations of the smart drill guide 104 can include a display 111, which can provide information to a user. Such information can include measurements and features associated with the drilled hole, such as how deep the drilled hole is and/or what type of tissue is being drilled into. For example, the processor 116 can process information collected from the sensing circuit 114 and/or a measuring feature (e.g., a sensor) and determine one or more characteristics associated with the drilled hole (e.g., drill depth, tissue type being drilled into, etc.) which can be communicated to the user via the display 111. The display 111 can also be a user interface that allows, for example, user input, such as for programming the smart drill guide 104. For example, some implementations of the display 111 can allow a user to input a start position (i.e., a zeroed location from which depth of the hole can be measured from) and/or an end location (e.g., a depth of the hole) of the drill relative to the tissue to be drilled into.

Some implementations of the smart drill guide 104 can include an alarm 113 that can provide warnings or feedback to the user. For example, when the processor 116 determines that the drill depth is approaching a desired depth or a tissue interface, the alarm can provide an alert (such as an audio or visual alert). Such desired depths and/or tissue interfaces, for example, can be programmed into the smart drill guide 104 by the user, such as through the display 111 associated with the smart drill guide 104.

Various embodiments of the drill depth measuring system are described herein which describe various features that can assist with determining the depth of the drill bit 110 into tissue, such as bone, as will be described in greater detail below. Although the drill depth measuring system is described herein as being used to drill and create a hole in bone tissue, other types of tissue can be used.

In addition to the above feature for detecting, via the sensing circuit, a capacitance and/or resistance in the tissue to which the drill bit is drilling into for determining a type of tissue being drilled into, an approaching tissue interface, and/or a drilled hole depth, other measuring features can be included in the drill depth measuring system. Such measuring features are described in greater detail below. Alternatively, any one of the measuring features can be included in the drill depth measuring system alone or in combination with other measuring features, such as for providing optional or additional ways for determining drill depth into tissue.

Figure 3:
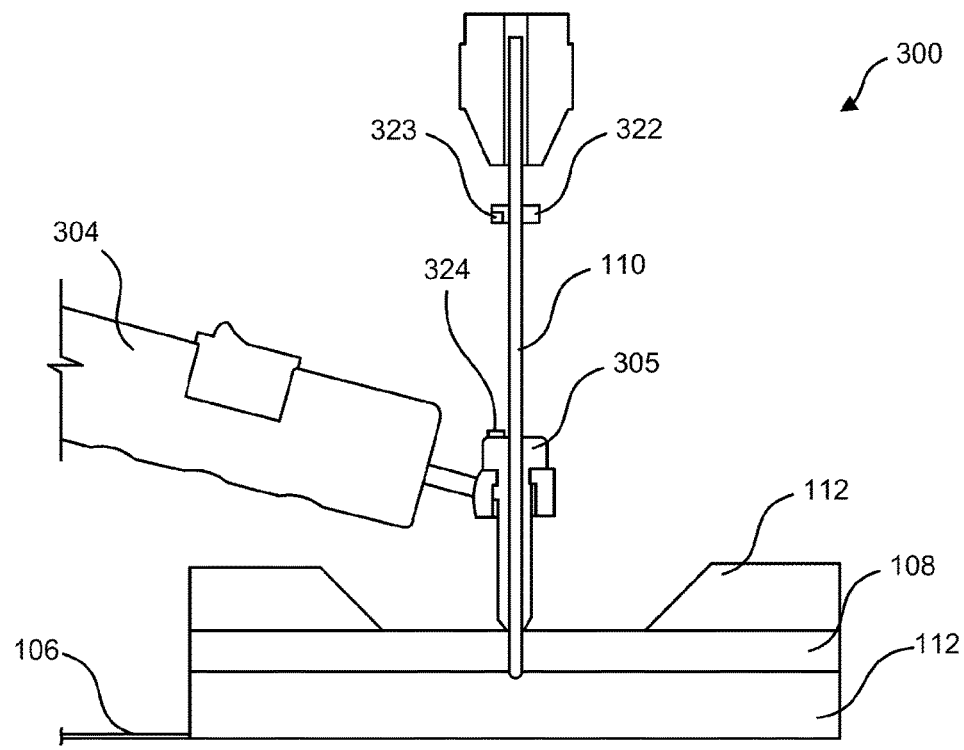
FIG. 3 shows an embodiment of the drill depth measuring system including a Hall Effect sensor.

FIG. 3 illustrates an embodiment of the drill depth measuring system 300 including a measuring feature that includes a Hall Effect sensor 324. In addition, the measuring feature can include a mounting feature 322 that includes a magnet 323, which can be coupled to the drill bit 110. For example, the mounting feature 322 can be disc shaped for coupling to an outer circumference of the drill bit 110. The Hall Effect sensor 324 can be coupled to a part of the smart drill guide 304, such as the drill guide feature 305 (as shown in FIG. 3), and can be positioned such that it can sense a magnetic field from the magnet 323. The Hall Effect sensor 324 can vary an output voltage in response to a magnetic field, which can be provided by the magnet 323. As such, as the distance between the magnet 323 and the Hall Effect sensor 324 change, so does the Hall Effect sensor's detection of the magnetic field. For example, the magnetic field provided by the magnet 323 can increase as distance between the Hall Effect sensor 324 and the magnet 323 decrease (and vice versa). The change in output voltage can be processed by the processor, which can be used to determine a distance between the Hall Effect sensor 324 and the mounting feature 322 or magnet 323.

The end of the drill bit 110 relative to the mounting feature 322 or magnet 323 can be known by the processor, such as entered into a user interface associated with the smart drill guide 304. A distance between the Hall Effect sensor 324 and a top surface of the bone 108 can also be known, such as via detection by other detection sensors or via user input. Therefore, as the drill bit 110 advances through the drill guide feature 305, the Hall Effect sensor 324 can detect and measure the magnet 323 moving closer, which can be used to determine a drill depth into the bone. Various placements of the Hall Effect sensor 324 and/or magnet 323 have been contemplated and are not limited to what is described and/or shown. For example, the Hall Effect sensor 324 can be positioned on a handle of the drill.

Figure 4:
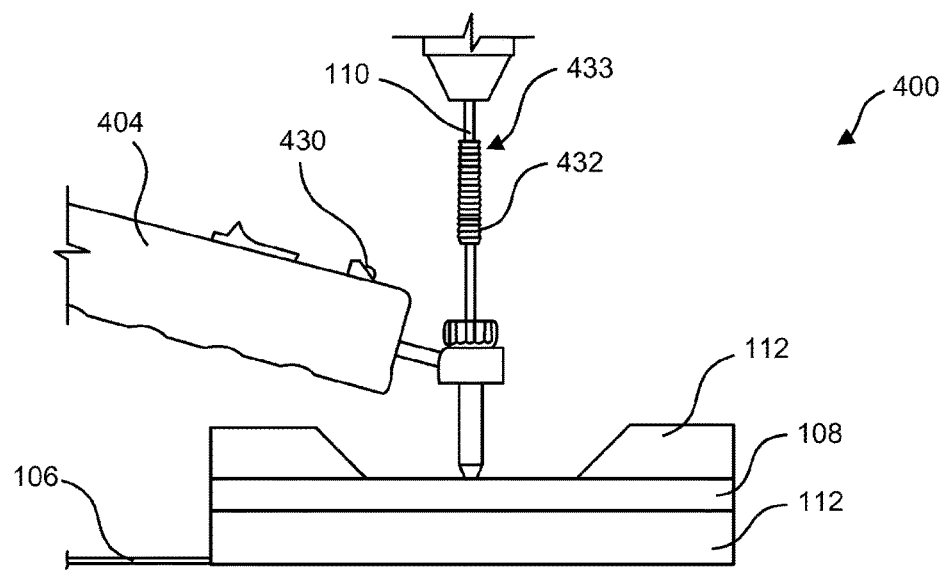
FIG. 4 shows an embodiment of the drill depth measuring system including an optical emitter/detector.

FIG. 4 illustrates an embodiment of the drill depth measuring system 400 including a measuring feature that includes an optical emitter/detector 430. The optical emitter/detector 430 can be positioned on the smart drill device 404 such that it can detect one or more markings 432 positioned along the drill bit 110 or along a sleeve 433 coupled to the drill bit 110 (as shown in FIG. 4). For example, each of the markings 432 along the sleeve 433 can correlate to a depth of the drill bit 110 in tissue. In some implementations, the optical emitter/detector 430 can emit light or capture an image for detecting the one or more markings 432 along the sleeve 433. As the drill bit 110 is advanced into tissue, the sleeve 433 can also advance the same distance in the direction of drilling. Therefore, a change in position of a marking 432 can be directly correlated to a change in drill bit depth. In addition or alternatively, each marking 432 can provide a measurement such that the optical emitter/detector 430 is reading or detecting a measurement associated with the marking 432 and not determining a change in position. Therefore, the optical emitter/detector 430 can either assist with determining a change in position of a marking, thereby determining a change in drill depth, or detect and relay a measurement associated with a marking 432 that provides a drill depth measurement.

Figure 5A:
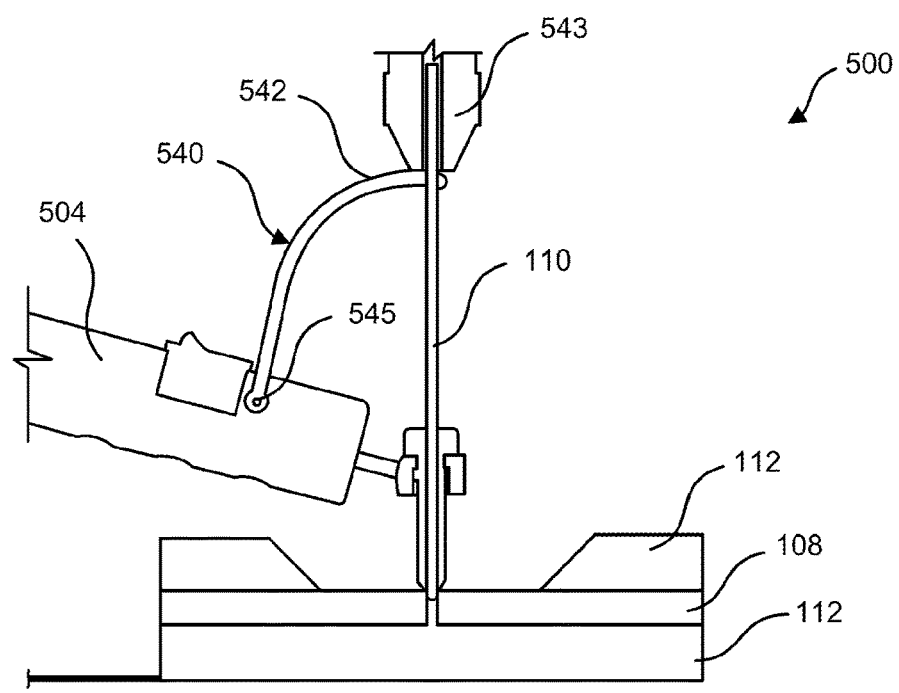
FIGS. 5A and 5B show an embodiment of the drill depth measuring system including a rotary movement sensor.
Figure 5B:
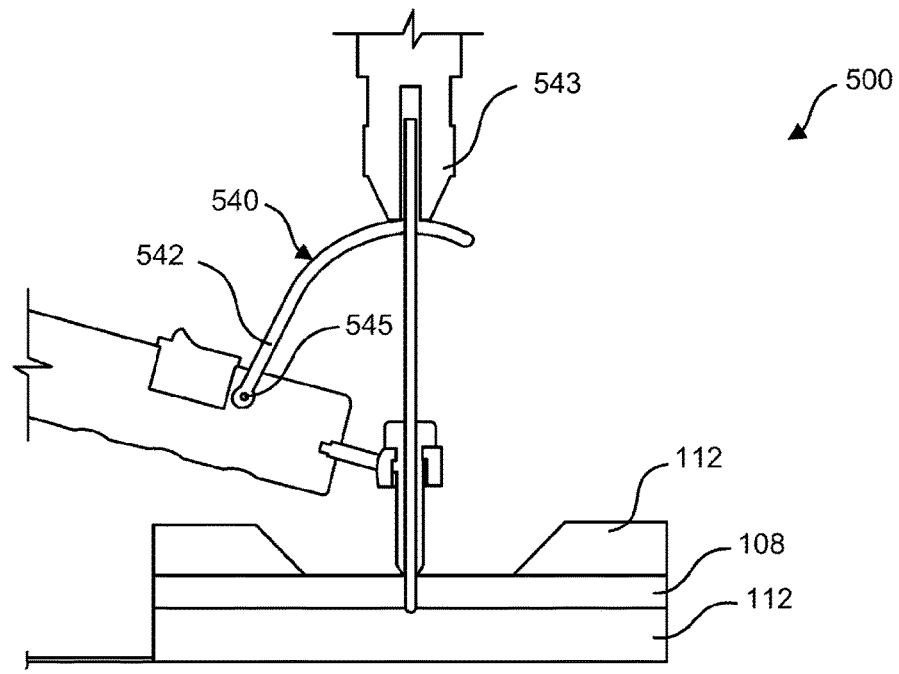

FIGS. 5A and 5B illustrate an embodiment of the drill depth measuring system 500 including a measuring feature that includes a rotary movement sensor 540 having a lever 542 that is pivotally coupled to the smart drill guide 504 at a proximal end. In addition, a distal end or part of the lever 542 can be placed in contact with a drill chuck 543 of the drill device. As such, when the drill chuck 543 advanced towards the tissue, such as during drilling of the hole into the tissue, the lever 542 can be forced to rotate. For example, z-axis displacement of the drill bit can be translated into rotary movement of the lever 542, as shown in FIG. 5B. Rotation of the lever 542 can be sensed by a sensor 545 associated with the smart drill guide 504, which can use such sensed information to determine the z-axis displacement of the drill bit, and thus the drill depth. The lever 542 can be curved or straight and can be spring loaded such that it is forced against the drill chuck 543.

Figure 6:
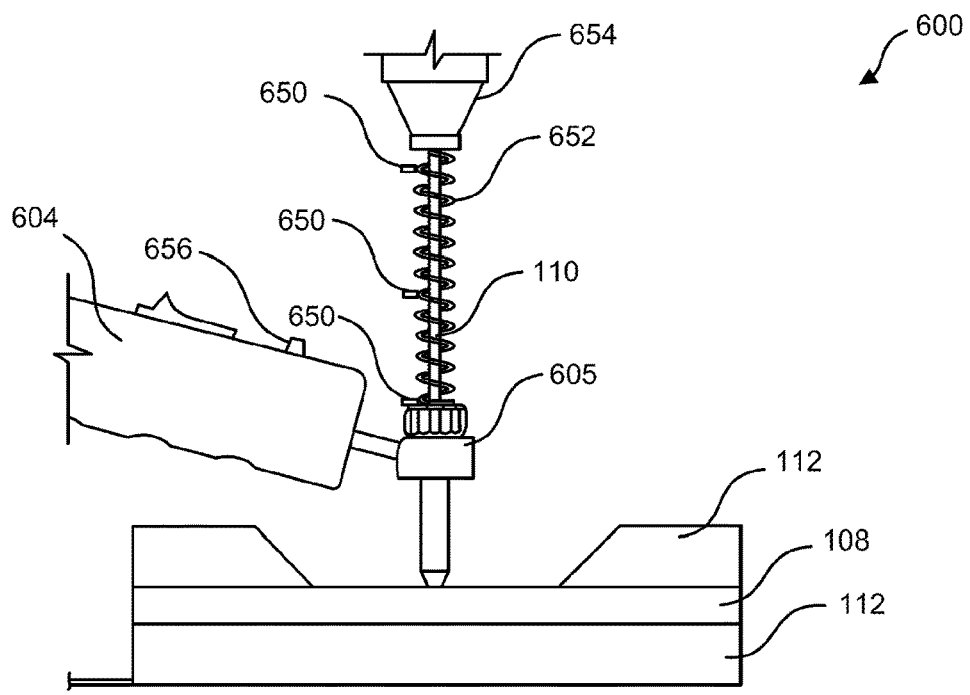
FIG. 6 shows an embodiment of the drill depth measuring system including potential sensor locations.

FIG. 6 illustrates an embodiment of the drill depth measuring system 600 including locators 650 that are positioned along a spring 652 extending between the drill chuck 654 and the drill guide feature 605. For example, a location sensor 656 can detect the position of at least one locator 650. In addition, the location sensor 656 can continue to detect the position of the at least one locator 650, including during advancing the drill bit 110 into bone 108. During such advancement, for example, the spring 652 can compress and the locators 650 can become closer together. The displacement of the locators 650 can be detected by the location sensor 656, which can be processed by the processor for determining a drill depth.

Figure 7:
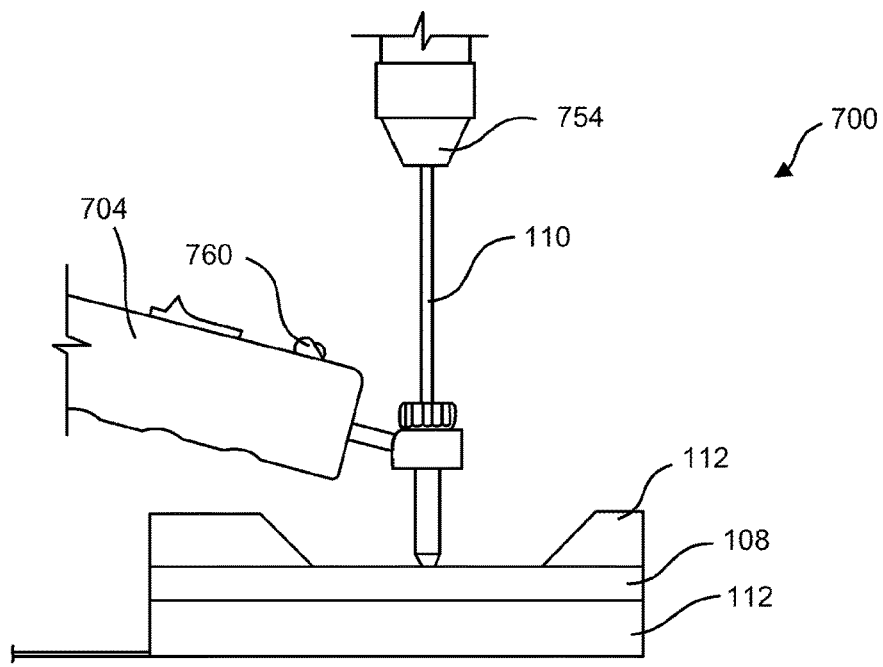
FIG. 7 shows an embodiment of the drill depth measuring system including a camera.

FIG. 7 illustrates an embodiment of the drill depth measuring system 700 including a camera 760. The camera 760 can be used with image processing software that can recognize parts of the drill and/or drill bit 110 in order to detect their movement and thereby determine a depth that the drill bit 110 has advanced into bone 108. The software can collect data from the camera 760 and/or from the processor associated with the smart drill guide 704. For example, images captured by the camera 760 depicting an edge of the drill chuck 754 can be converted by the software and processor into drill depth readings. Such readings can be displayed on a display associated with the drill guide for user viewing.

For example, as shown in FIG. 7, the camera 760 can be coupled to the smart drill guide 704 and have a fixed focal length view that captures the entire movement of the drill chuck. In addition, a location, such as an edge of the drill chuck, captured by the camera can be converted into a z-axis depth (i.e., depth of the drill bit into tissue).

Figure 8:
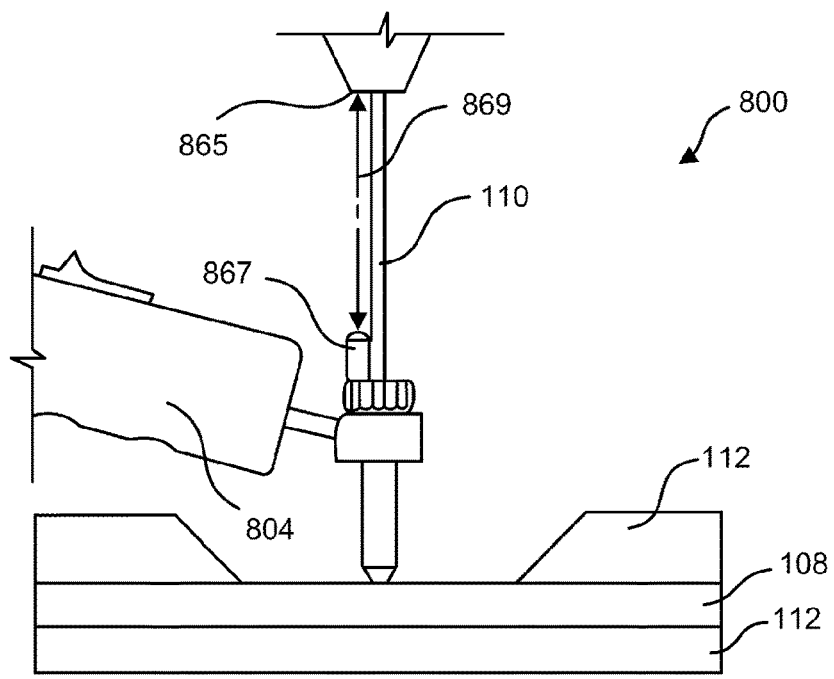
FIG. 8 shows an embodiment of the drill depth measuring system including a reflective surface and an emitter/detector.

FIG. 8 illustrates an embodiment of the drill depth measuring system 800 including a reflective surface 865 and an emitter/detector 867. For example, the emitter/detector 867 can emit light 869 to the reflective surface 865, which can be detected by the emitter/detector 867. Various factors related to the reflection (e.g., time, etc.) can be used to determine a distance between the emitter/detector 867 and the reflective surface 865, which can be used to determine a depth of the drill bit 110 into tissue. For example, the distance between the emitter/detector 867 and bone 108 can be fixed. A change in distance between the emitter/detector 867 and the reflective surface 865 can correlate to the distance the drill bit 110 has advanced into the bone. Such determinations can be processed by the processor of the smart drill guide 804 and displayed on a display associated with the smart drill guide 804.

Figure 9:
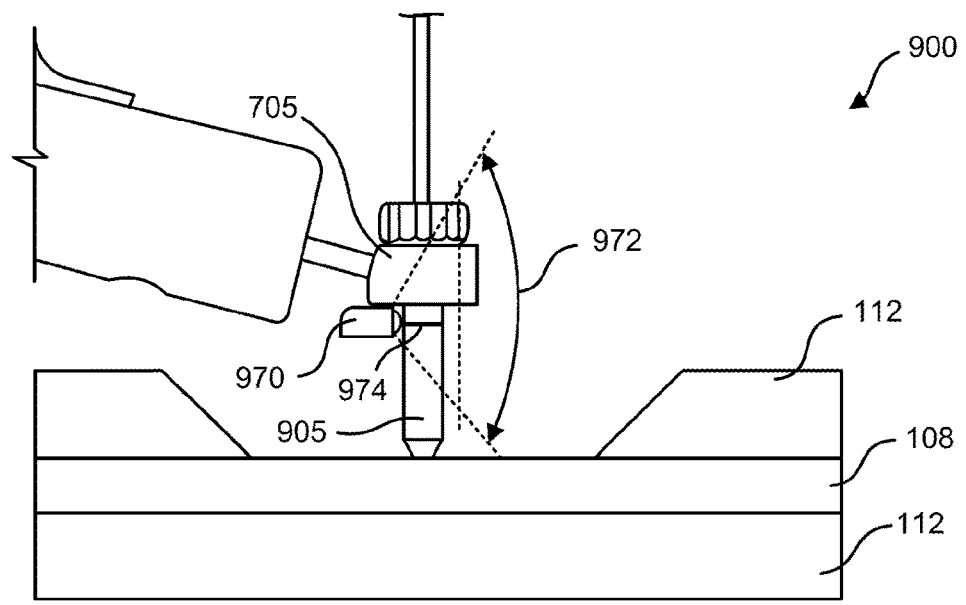
FIG. 9 shows an embodiment of the drill depth measuring system including a flute detecting camera.

FIG. 9 illustrates an embodiment of the drill depth measuring system 900 including a flute detecting camera 970. For example, a view port can be machined into the drill guide feature 705 to allow optical and/or electrical sensing of the presence or lack of flutes 974. The flute detecting camera 970 can have a fixed focal length and angle 972 that can allow for the tracking of the movement of the flutes 974, such as in a vertical or drilling direction, which can be used to determine drill bit depth.

Figure 10:
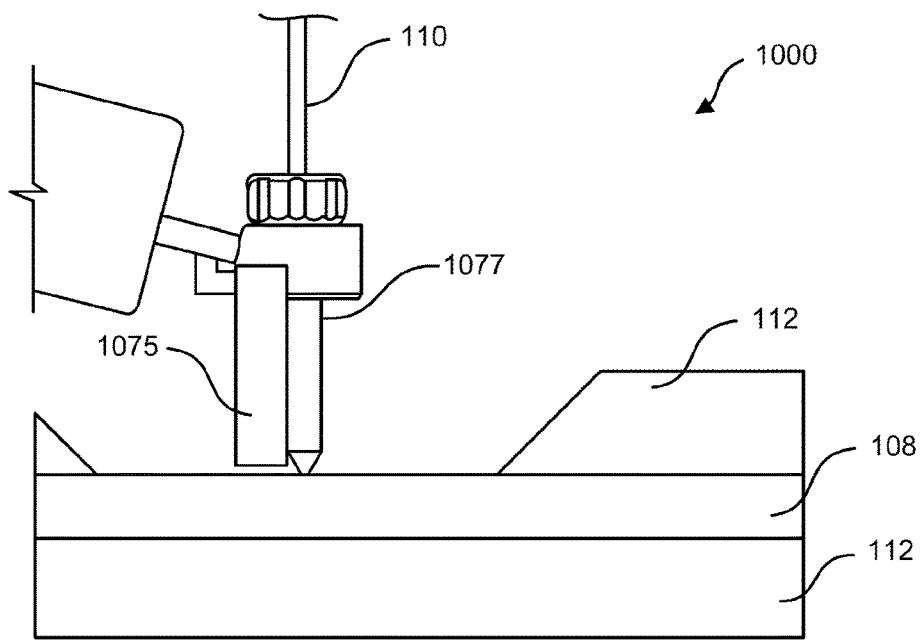
FIG. 10 shows an embodiment of the drill depth measuring system including an array of sensors for sensing the presence or lack of flutes based on signal properties.

FIG. 10 illustrates an embodiment of the drill depth measuring system 1000 including an array of sensors 1075 for sensing the presence or lack of flutes 1077 along the drill bit 110, such as by detecting a flute end. Such detection can be based on signal properties picked up by the array of sensors 1075, such as changes in surface features resulting in changes in optical imaging and/or reflection. In addition, such detection can allow for the tracking of the movement of the flutes 1077, such as in a vertical or drilling direction, which can be used to determine drill bit depth.

Figure 11:
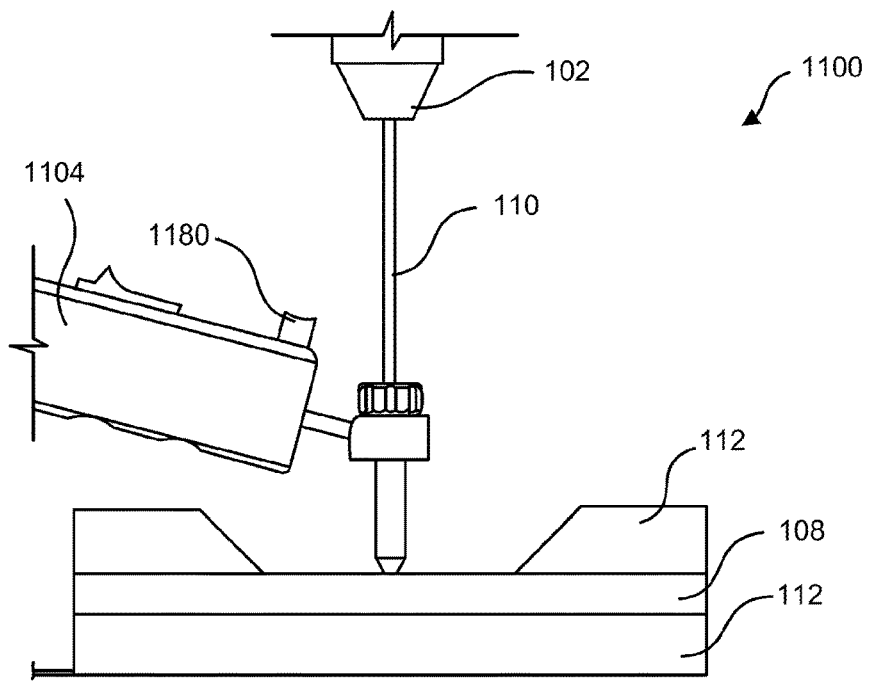
FIG. 11 shows an embodiment of the drill depth measuring system including a microphone, such as for sensing volume and audio properties associated with drill noise.

FIG. 11 illustrates an embodiment of the drill depth measuring system 1100 including a microphone 1180 that can sense volume and audio properties associated with drill noise. For example, the microphone 1180 can collect audio frequency and/or amplitude data, which can be interpreted by the processor of the smart drill guide 1104. As such, the processor can process such collected audio data and determine a distance of advancement of the drill bit 110 into tissue. For example, an increase in frequency and/or amplitude can indicate an increase in z-axis advancement of the drill bit 110 into bone 108. The microphone 1180 can be coupled to the smart drill guide 1104 such that the position of the microphone 1180 relative to the bone 108 and/or relative to the drill 102 is known. As such, displacement of the drill 102 relative to the microphone 1180 can be used to determine a drill depth.

Figure 12:
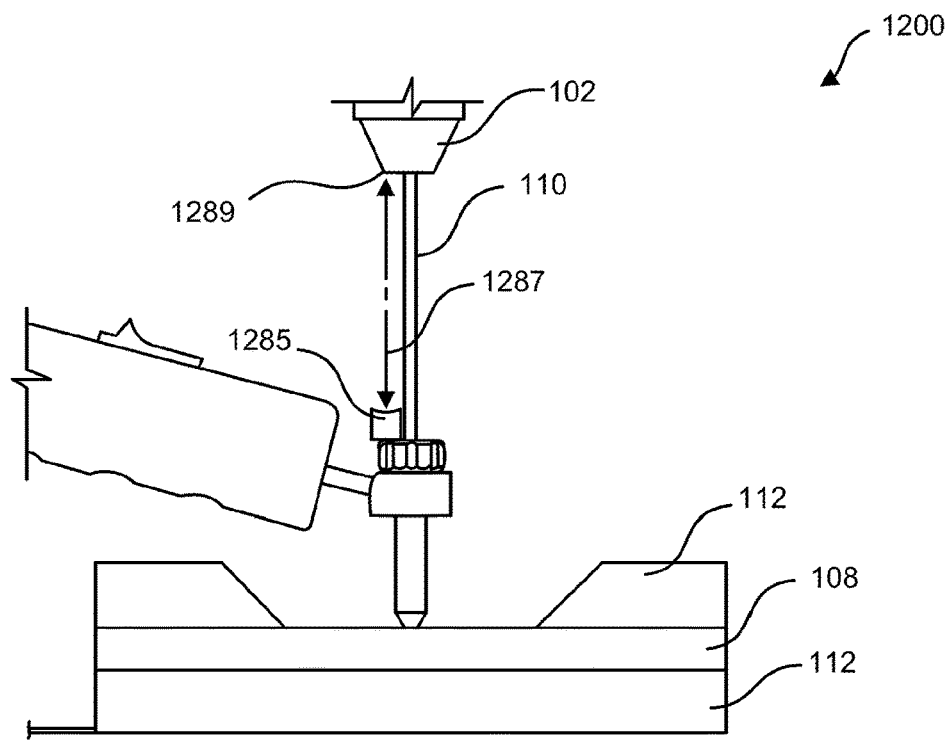
FIG. 12 shows an embodiment of the drill depth measuring system including a piezo element.

FIG. 12 illustrates an embodiment of the drill depth measuring system 1200 including a piezo element 1285, which can use ultrasonic depth detection. For example, the piezo element 1285 can emit and detect acoustic waves 1287 in order to determine location of a reflective surface 1289, which can be associated with the drill 102 and/or drill bit 110.

Additional features and methods associated with the drill depth measuring system can include a conductive tip of the drill (e.g., test tissue properties adjacent drill bit), a cannulated drill bit with fiber optics down the center (e.g., enable seeing material adjacent to drill bit), and features for measuring resistance of the drill bit at more than one point (e.g., compare readings).

Figure 13:
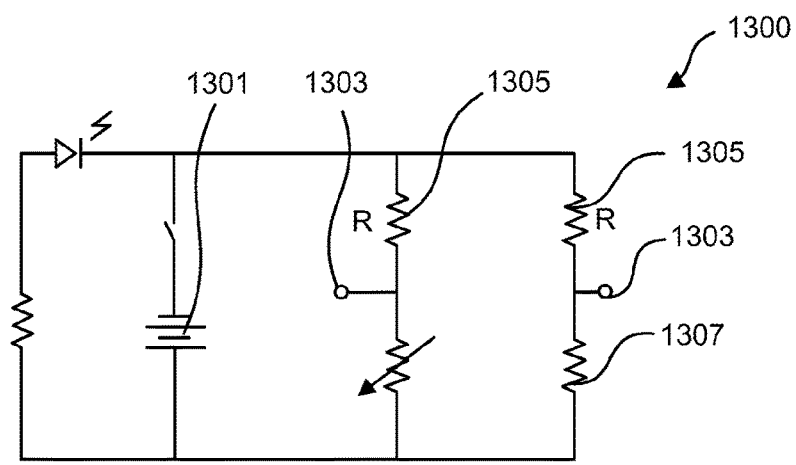
FIG. 13, shows a Wheatstone bridge that can be included in a circuit of the drill depth measuring system for measuring resistance.

At least some embodiments of the drill depth measuring system can measure changes in resistance and/or capacitance, including at a bone-soft tissue interface. For example, as shown in FIG. 13, a Wheatstone bridge 1300 can be included in a circuit of the drill depth measuring system for measuring resistance. By way of further example, as shown in FIG. 13, the Wheatstone bridge 1300 can include a DC power supply 1301 and analog inputs 1303 can be wired on Arduino Uno. Signal drilling from bone to tissue can be compared using different resistance values for the two R resistors 1305. For example, 500 kΩ, 5 kΩ, and 1 MΩ can be used. A tissue resistor 1307 can include the resistance qualities of the tissue that is being drilled into by the drill depth measuring system. The resistance of a light (Rled) and a resistance of a potentiometer (Rpot) can also be included in the Wheatstone bride 1300, which can assist with tuning.

Figure 14:
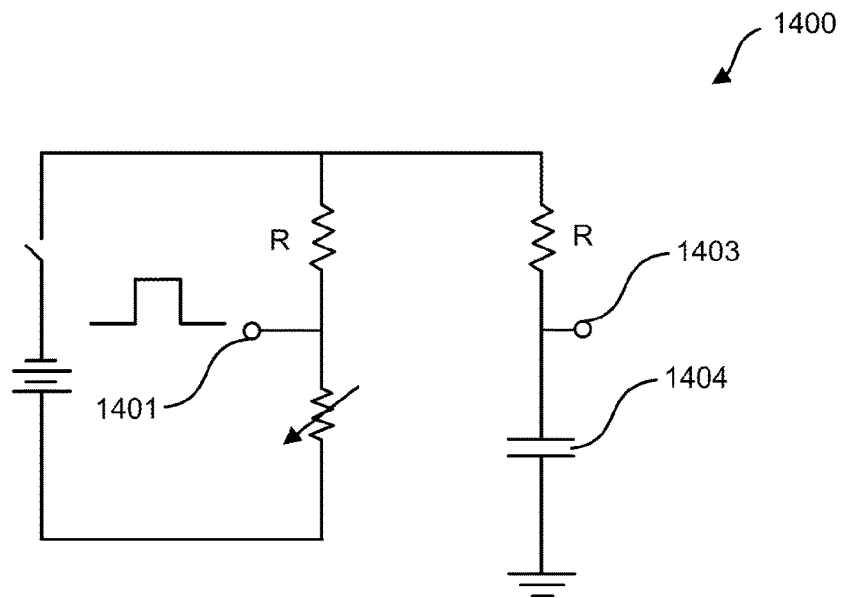
FIG. 14 illustrates an example capacitive circuit that can be included in the drill depth measuring system for measuring capacitance.

FIG. 14 illustrates an example capacitive circuit 1400 that can be included in the drill depth measuring system, such as the smart drill guide, for measuring capacitance. The capacitive circuit 1400 can be pulsed at a first digital input 1401 and compared to a second digital input 1403. By comparing the charging and discharging rate of the second digital input 1403, the capacitive time constant of the tissue and/or bone 1404 can be calculated, such as via the processor. In addition, it has been contemplated that any time varying voltage can be used.

Figure 15:
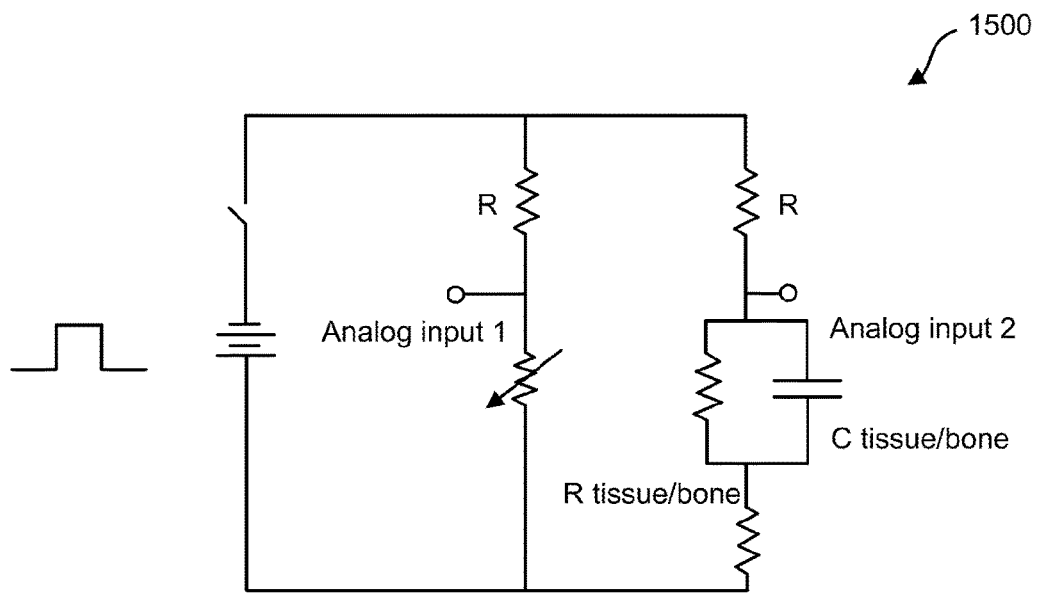
FIG. 15 illustrates an example RC circuit that can be included in the drill depth measuring system for measuring both resistive and capacitive properties of tissue.

FIG. 15 illustrates an example resistor-capacitor (RC) circuit 1500 that can be included in the drill depth measuring system, such as the smart drill guide, for measuring both resistive and capacitive properties of tissue. The RC circuit 1500 can be used to signal the tissue-bone interface relative to the position of the drill bit. Both signals can be analyzed by the processor and specific points in the resistivity profile can be matched up with the depth of the drill bit. This information can be compared to the mechanically measured depth of the bone.

The transmitted signal can be one or more of a simple direct current (DC) voltage, DC pulse, pulse width modulated DS signal, alternating current (AC), which can allow for discrimination between electrical signals and identify the electrical signal of interest. Some waveforms can also allow for enhanced signal transmission and detection. The input and/or output of the sensors can be conditioned and/or processed by the circuitry (which can include a Controller, Programmed Logic Array (PLA), or Microprocessor) to produce an output signal that can be one or more of an analog, digital, square wave, curve-fit, averaged, clipped, smoothed, noise reduced, or otherwise processed or amplified in order to optimize interpretation of the data representing the real-time position of the drill relative to the tissue.

Figure 16:
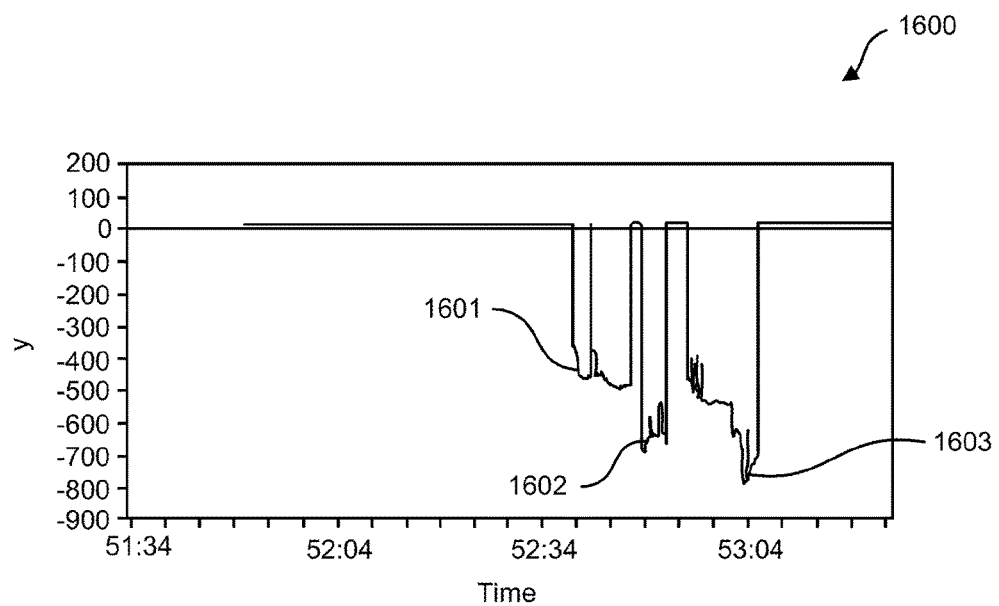
FIG. 16 illustrates an example measured resistance graph from drilling into tissue.

FIG. 16 illustrates an example first graph 1600 showing measured resistances (y-axis) over time (x-axis) from drilling into tissue. The first graph 1600 shows changes in resistance as the drill advances through tissue. For example, as the drill starts at the bone level, there can be a sharp change in signal as the drill enters the meat or flesh level. As shown in FIG. 16, the first valley 1601 can be a result of drilling into bone, the second valley 1602 can be a result of drilling into meat or flesh, and the third valley 1603 can be a result of drilling from bone to meat or flesh.

Figure 17:
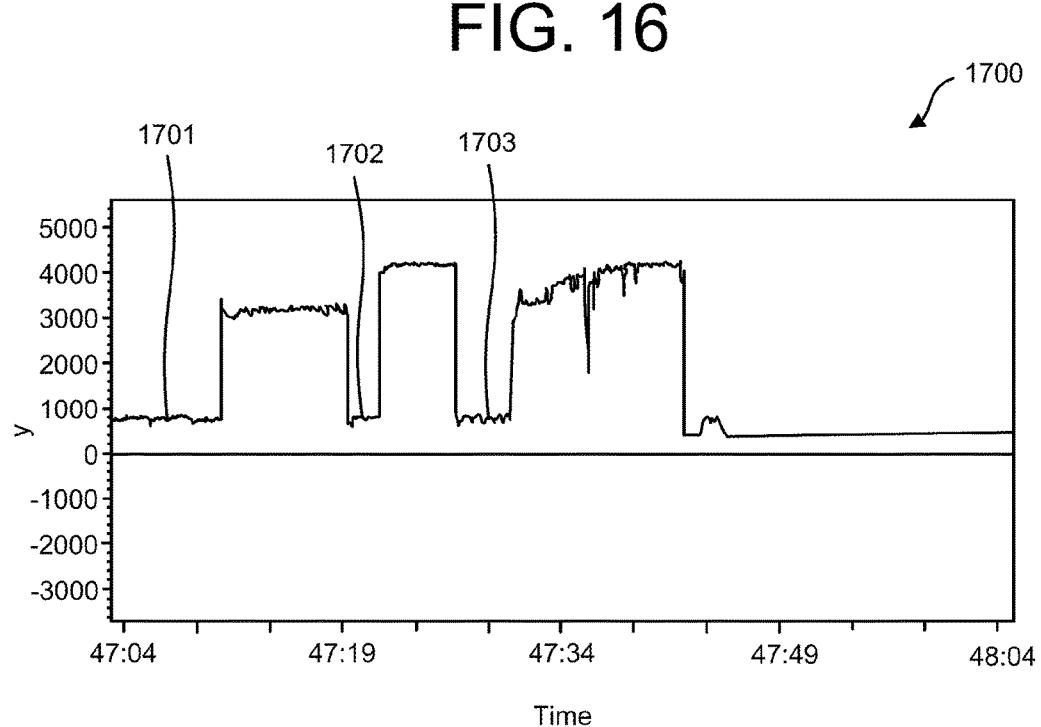
FIG. 17 illustrates an example measured capacitance graph from drilling into tissue.

FIG. 17 illustrates an example second graph 1700 showing measured capacitances (y-axis) over time (x-axis) from drilling into tissue. The second graph 1700 shows changes in capacitance as the drill advances through tissue. As shown in FIG. 17, the first valley 1701 can be a result of drilling into bone, the second valley 1702 can be a result of drilling into meat or flesh, and the third valley 1703 can be a result of drilling from bone to meat or flesh.

In addition, a circuit with appropriate filtering can take advantage of both resistive and capacitive signals. Also, signals (i.e., resistive, capacitive) can directly correspond to drill depths in tissue, which can be processed using the processor associated with the smart drill guide. This can allow resistance and/or capacitance readings to directly indicate to a user the depth of the drill bit into tissue, such as bone. Furthermore, rate changes in acquired signals as a function of distance can be used to determine the depth at which a drill bit has advanced into bone.

At least some embodiments of the drill depth measuring system can include a light feature that can shine light on tissue and measure the intensity of the reflected light. For example, bone can reflect more light than soft tissue. As such, by determining or analyzing the amount of light reflected, the drill depth measuring system can determine the type of tissue being shone on. In some embodiments, a fiber optic can provide light to be shone on the tissue.

Figure 18:
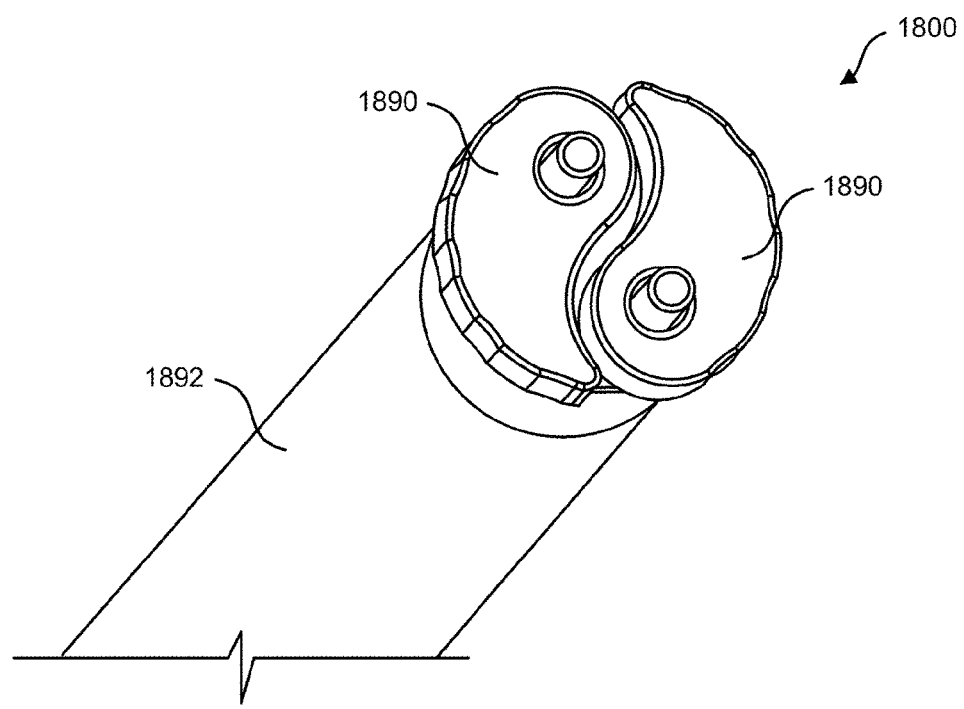
FIG. 18 shows an embodiment of an expanding-disc style gauge in the closed position.
Figure 19:
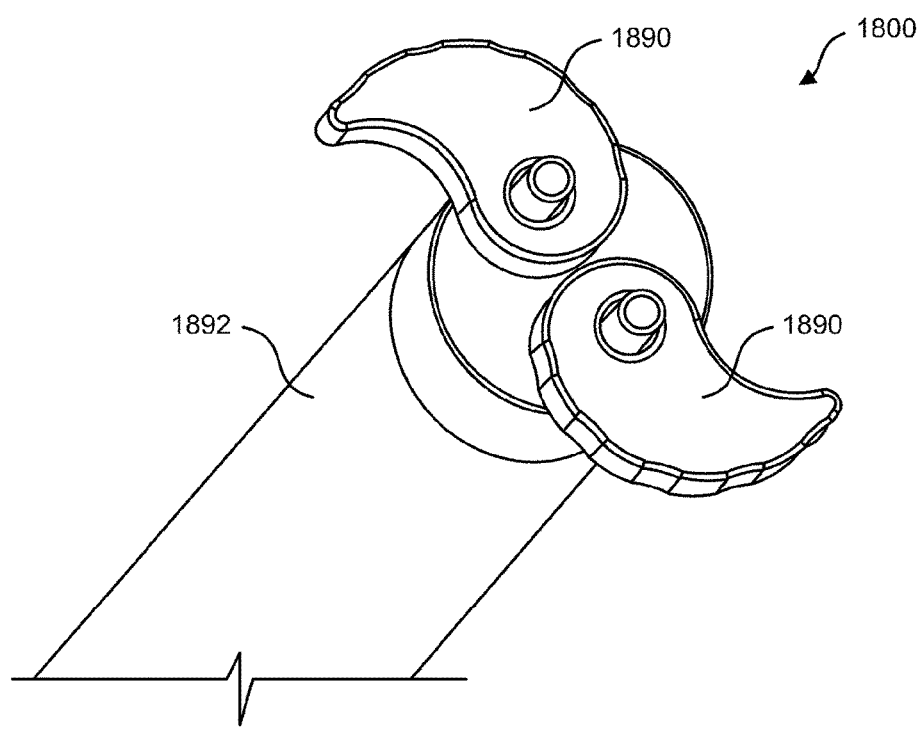
FIG. 19 shows the expanding disc style gauge of FIG. 18 in an open position.

At least some embodiments of the drill depth measuring system can include one or more features for mechanically sensing a depth of a hole drilled into tissue, such as bone. For example, FIG. 18 shows an embodiment of an expanding gauge 1800 in a closed position. As shown in FIG. 18, the expanding gauge 1800 includes a pair of rotating elements 1890 that are pivotably coupled to a distal end of an elongated shaft 1892. In the closed position, the outer circumference of the rotating elements 1890 can be sized and shaped to allow for the rotating elements 1890 and at least a distal part of the elongated shaft 1892 to pass through a hole that has been drilled through tissue, such as bone 108. Once the rotating elements 1890 have been passed through the drilled hole, they can be expanded, as shown in FIG. 19. Once expanded, the user can pull back on the elongated shaft 1892, thereby catching a back surface of the rotating elements 1890 against a back side of the bone (i.e., the side of the bone surrounding the hole made through the bone (see example positioning in FIG. 25), which can then allow a user to determine a depth of the hole. For example, features or marks along the side of the elongated shaft 1892 can be used to assist in determining the depth of the hole. The rotating elements 1890 can be closed or collapsed in order to retract the expanding gauge 1800 from the hole. The rotating elements 1890 can be any number of shapes and sizes, such as circular, triangular, square, or any other shape, such as the curved shape of the rotating elements 1890 shown in FIG. 18, which have a rounded first end and a pointed second end.

Figure 20:
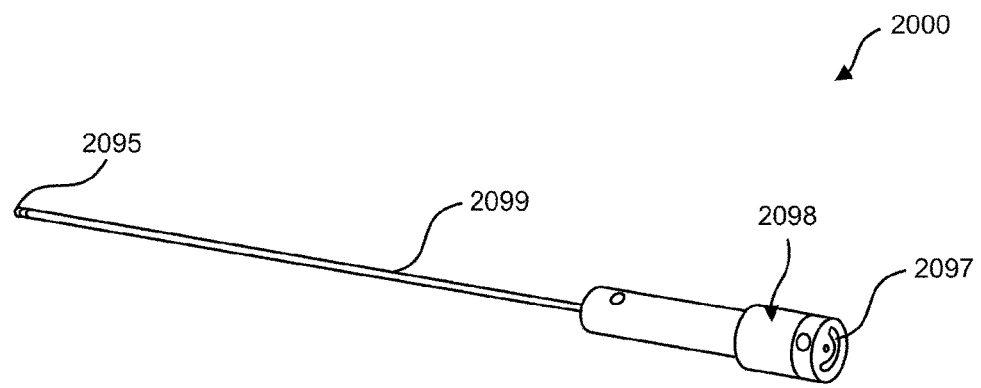
FIG. 20 shows an embodiment of a single-disc pivoting device.
Figure 21:
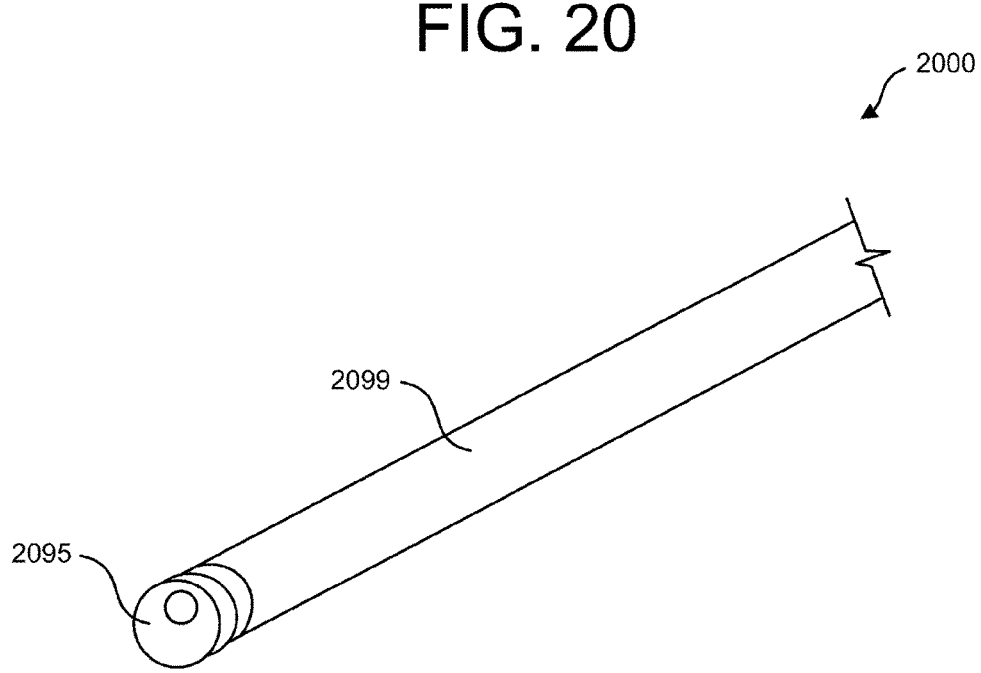
FIG. 21 shows a detail view of a distal tip of the single-disc pivoting device in the closed position.
Figure 22:
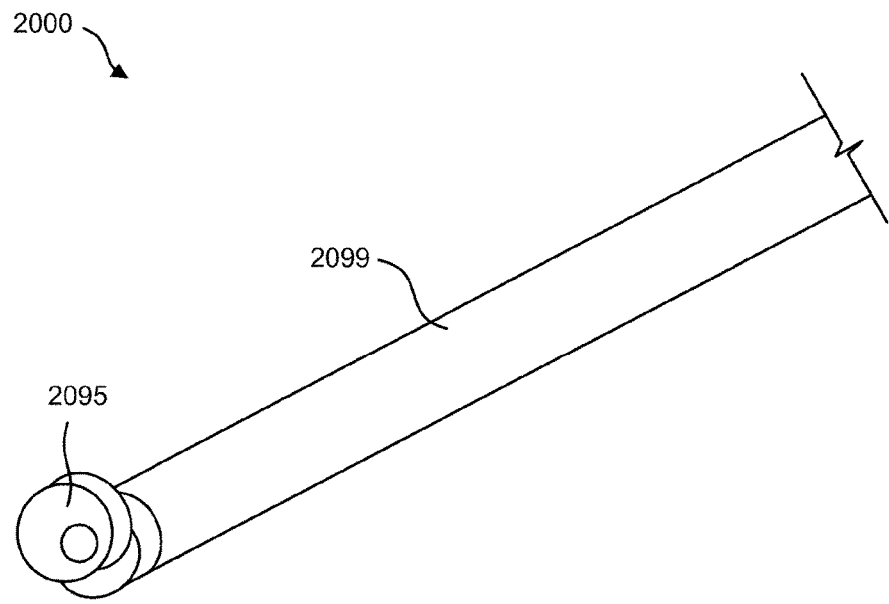
FIG. 22 shows a detail view of the distal tip of the single-disc pivoting device in the open position.
Figure 23:
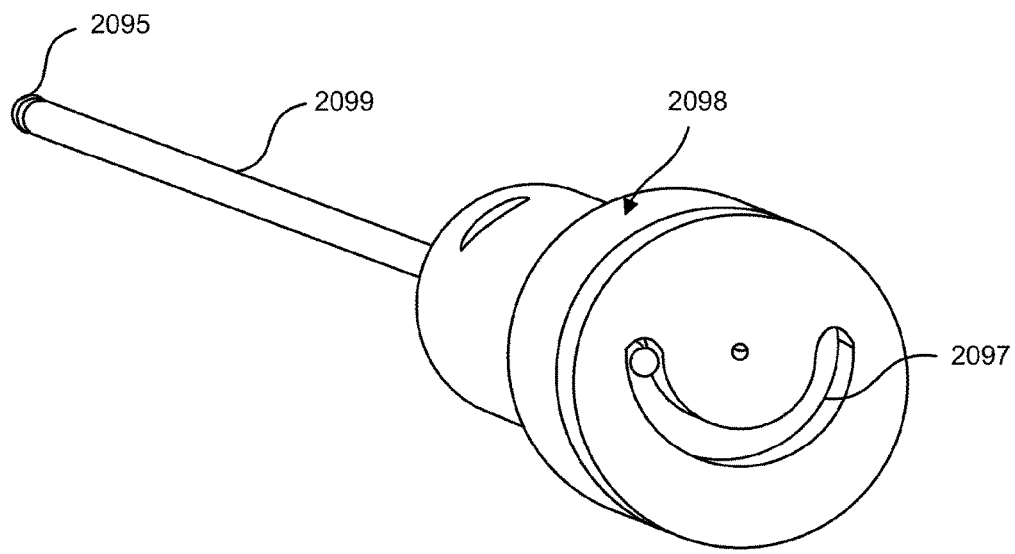
FIG. 23 shows an embodiment of a proximal end of a single-disc pivoting device showing an actuation mechanism in a closed position.
Figure 24:
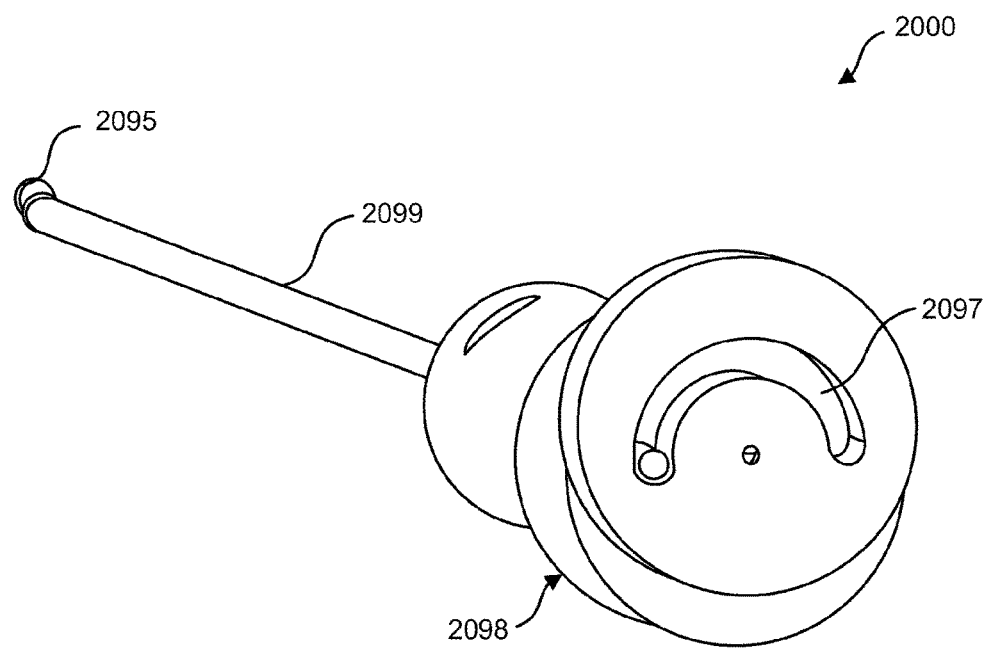
FIG. 24 shows the proximal end of the single-disc pivoting device with the actuation mechanism in an open position.

FIG. 20 shows an embodiment of a single-disc pivoting device 2000, which can include a single rotating element 2095 that can rotate or pivot at a distal end of an elongated shaft 2099. For example, rotation of a proximal feature 2098 can allow the single rotating element 2095 to rotate or pivot, such as off-center from the distal end of the elongated shaft 2099. A display 2097 can provide a user with an indication as to what position the single rotating element 2095 is in (i.e., closed or open). FIG. 21 shows the distal tip of the single-disc pivoting device 2000 in a closed position. FIG. 22 shows the distal tip of the single-disc pivoting device 2000 in an open position. FIG. 23 shows an embodiment of a proximal end of the single-disc pivoting device 2000 showing an actuation mechanism or proximal feature 2098 in a closed position. FIG. 24 shows the proximal end of the single-disc pivoting device 2000 with the actuation mechanism or proximal feature 2098 in an open position.

Figure 25:
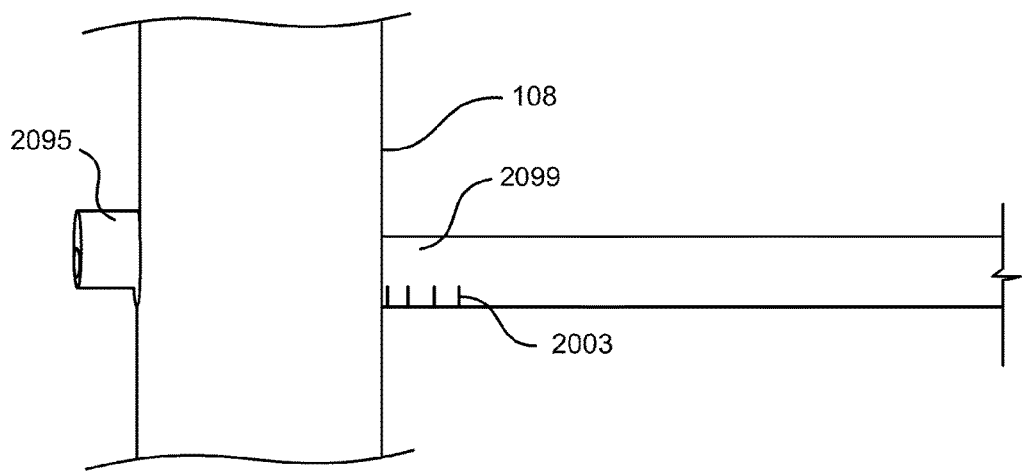
FIG. 25 shows a detail side view of the distal tip of the single-disc pivoting device in the open position.

FIG. 25 shows the distal tip of the single-disc pivoting device 2000 in the open position and capturing a back side of a bone 108 that the single-disc device 2000 is extending through (e.g., via a drilled hole). As shown in FIG. 25, one or more markings 2003 can be positioned along the elongated shaft 2099, which can provide reference points that the user can use for measuring the depth of the hole once the expanding gauge 1800 has been pulled back out of the hole. Alternatively or in addition, the markings 2003 can include dimensions that allow the user to directly measure the depth of the hole, such as while the pivoting device 200 is extending through the hole, as shown in FIG. 25.

Figure 26:
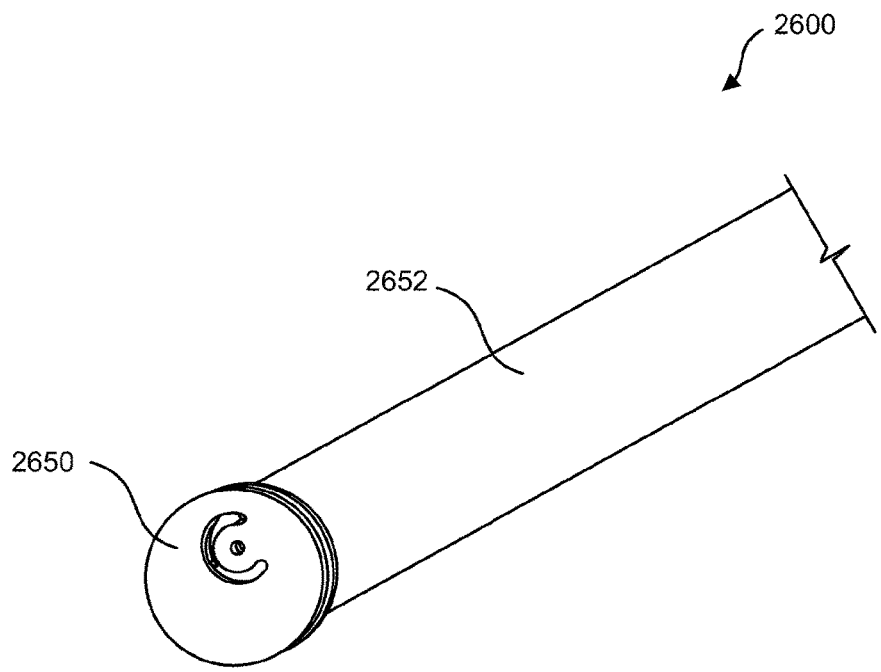
FIG. 26 shows an embodiment of a distal tip of a triple expanding disc device in a closed position.
Figure 27:
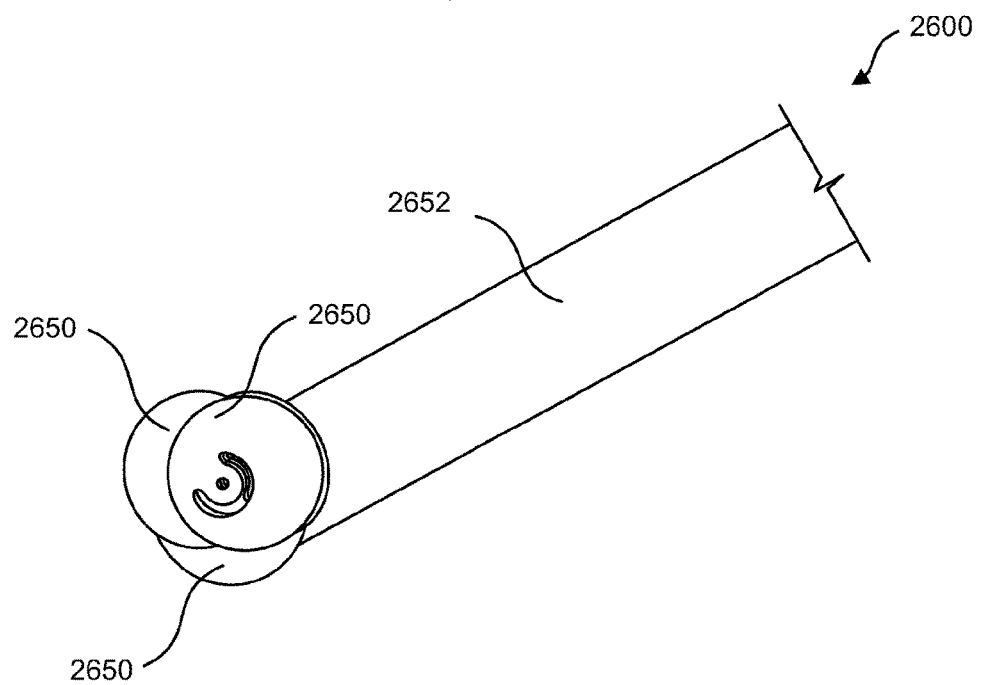
FIG. 27 shows the distal tip of the triple expanding disc device in an open position.
Figure 28:
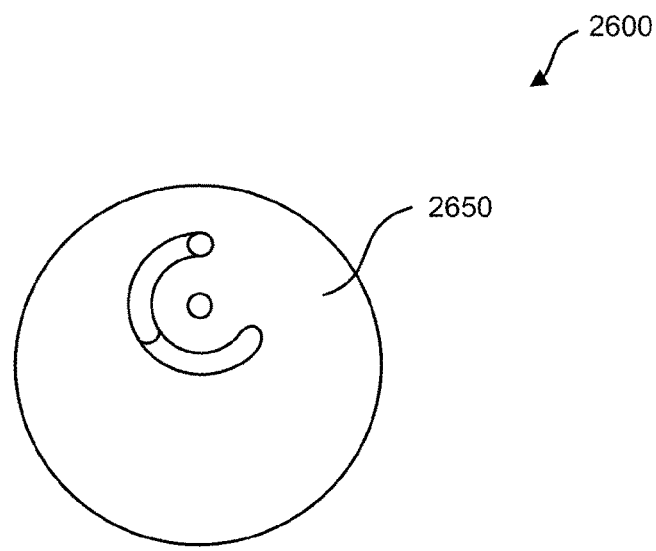
FIG. 28 shows an end view of the triple expanding disc device in a closed position.
Figure 29:
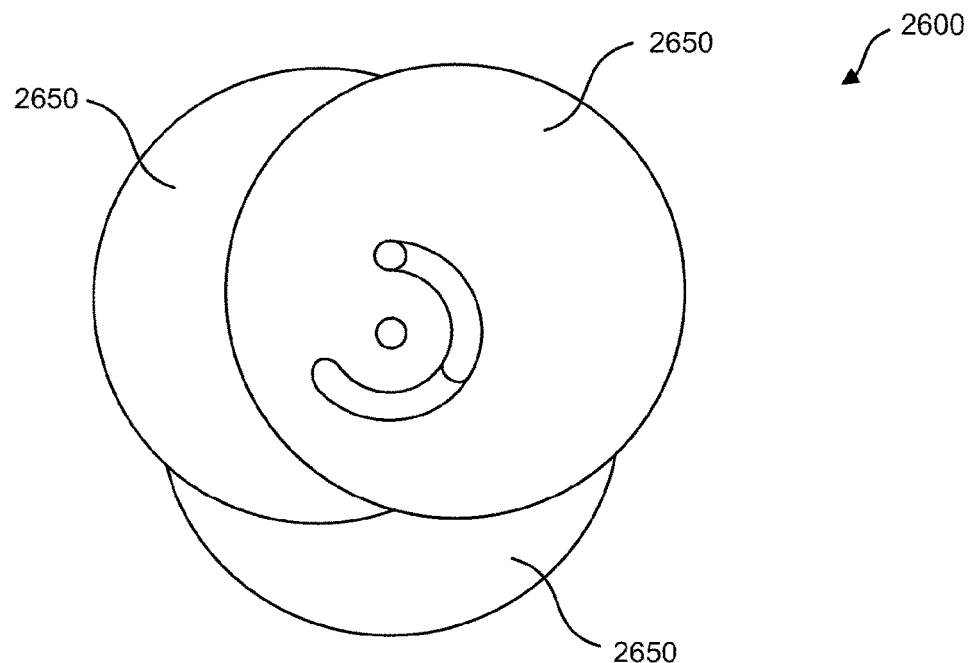
FIG. 29 shows an end view of the triple expanding disc device in an open position.
Figure 30:
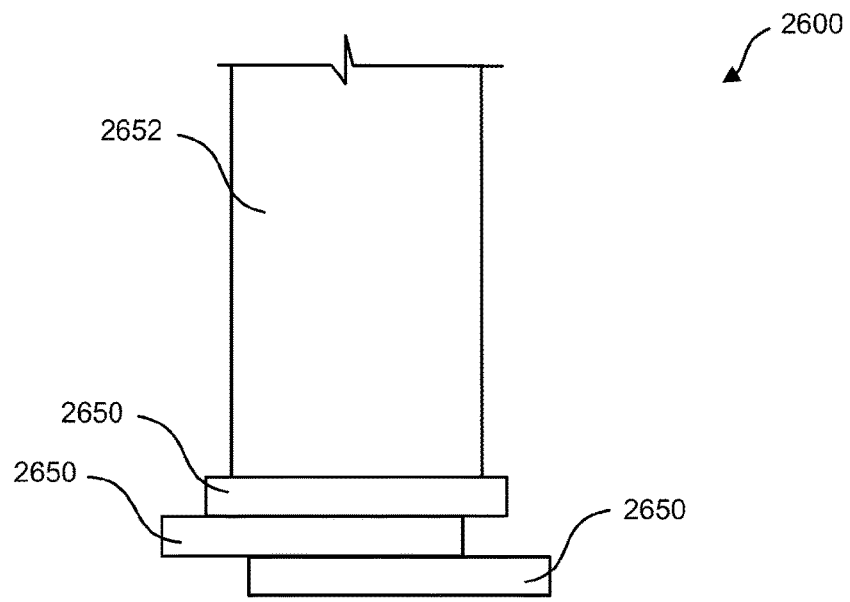
FIG. 30 shows a side-view of the distal end of the triple expanding disc device.

FIG. 26 shows an embodiment of a distal tip of a triple expanding disc device 2600 in a closed position, with the pivoting discs 2650 in a stacked position at a distal end of an elongated shaft 2652. The triple expanding disc device providing the same or similar features and functions as the above embodiments of the expanding disc device (i.e., expanding gauge 1800 and single-disc pivoting device 2000), however, with a different variation of the expanding feature (i.e., three discs that expand out from the circumference of the elongated shaft 2652). FIG. 27 shows the distal tip of the triple expanding disc device 2600 in an open position, with at the pivoting discs 2650 in an unstacked or spread-out configuration at a distal end of the elongated shaft 2652. FIG. 28 shows an end view of the triple expanding disc device 2600 in a closed position. FIG. 29 shows an end view of the triple expanding disc device 2600 in an open position. FIG. 30 shows a side view of a distal end of the triple expanding disc device 2600.

Figure 31:
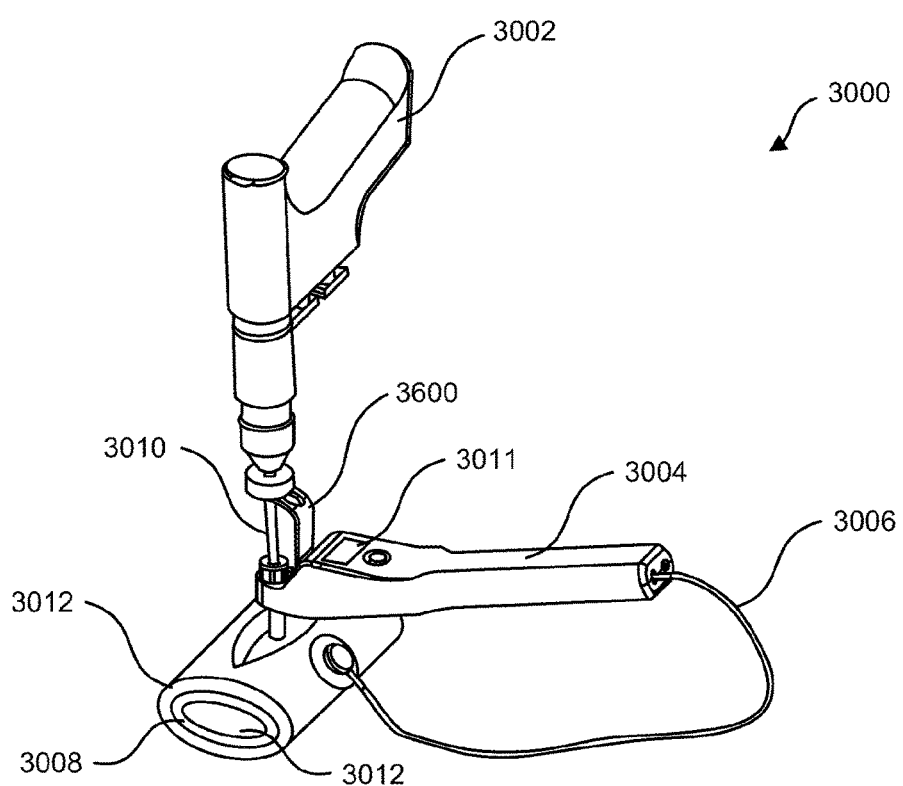
FIG. 31 shows an isometric view of another embodiment of drill depth measuring system.

FIG. 31 shows an embodiment of the drill depth measuring system, which can include any of the features associated with any of the drill depth measuring systems described herein. As shown in FIG. 31, the drill depth measuring system 3000 is shown with the grounding wire 3006 extending from the smart drill guide 3004 to tissue 3012 associated with a patient. The drill bit 3010 extending from the drill 3002 is in contact with bone 3008 located beneath the tissue 3012. The smart drill guide 3004 can detect either the capacitance or resistance of the tissue, including changes in either capacitance or resistance of the tissue as the drill bit is advanced into the bone (such as with a sensing circuit 114). These detections can be processed by the processor associated with the smart drill guide 3004, which can allow the processor to determine a drill depth of the drill bit into the bone and/or a type of tissue being drilled into. The drill depth and/or tissue type can be communicated to a user, such as via a display 3011 associated with the smart drill guide 3004. As such, a user can efficiently and precisely determine a drill depth made into the bone.

Figure 32:
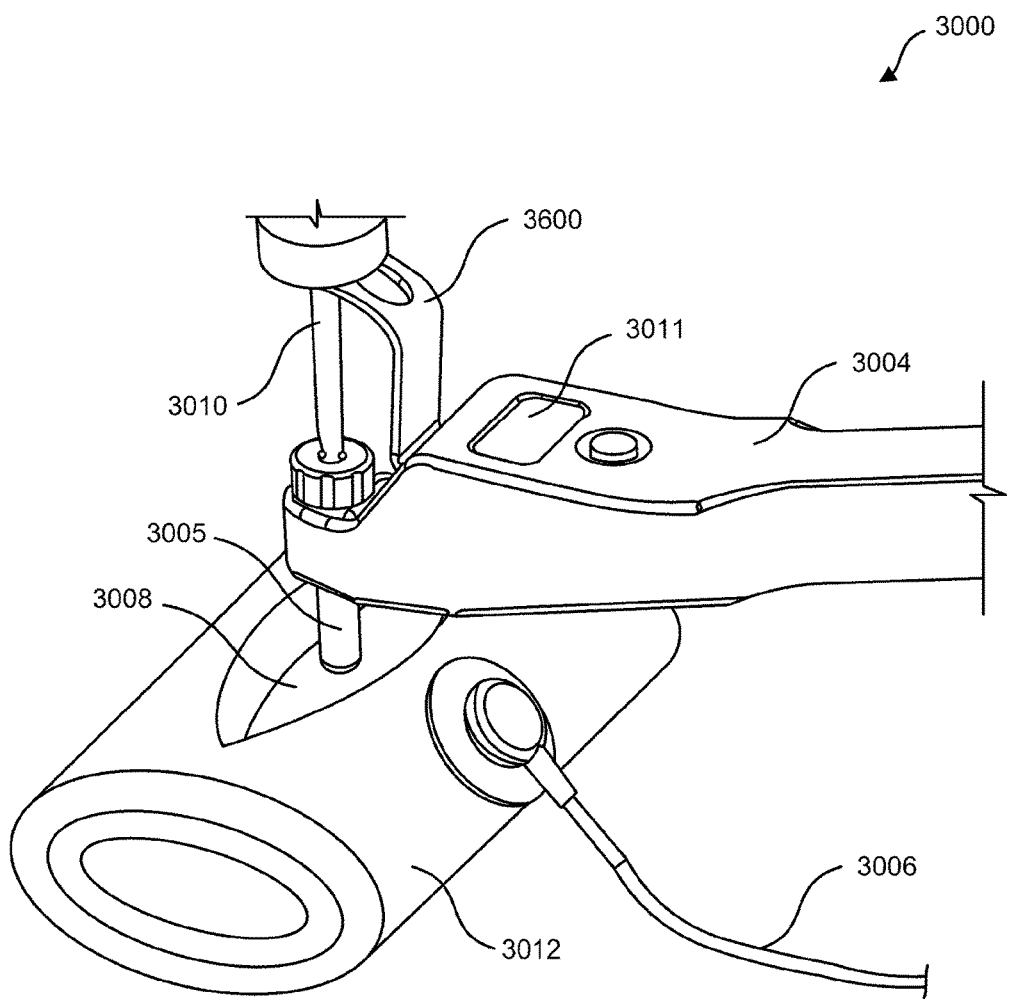
FIG. 32 shows a detail isometric view of the drill depth measuring system of FIG. 31 with the drill guide engaged with the bone/tissue representation with the electrode placed on the tissue.
Figure 33:
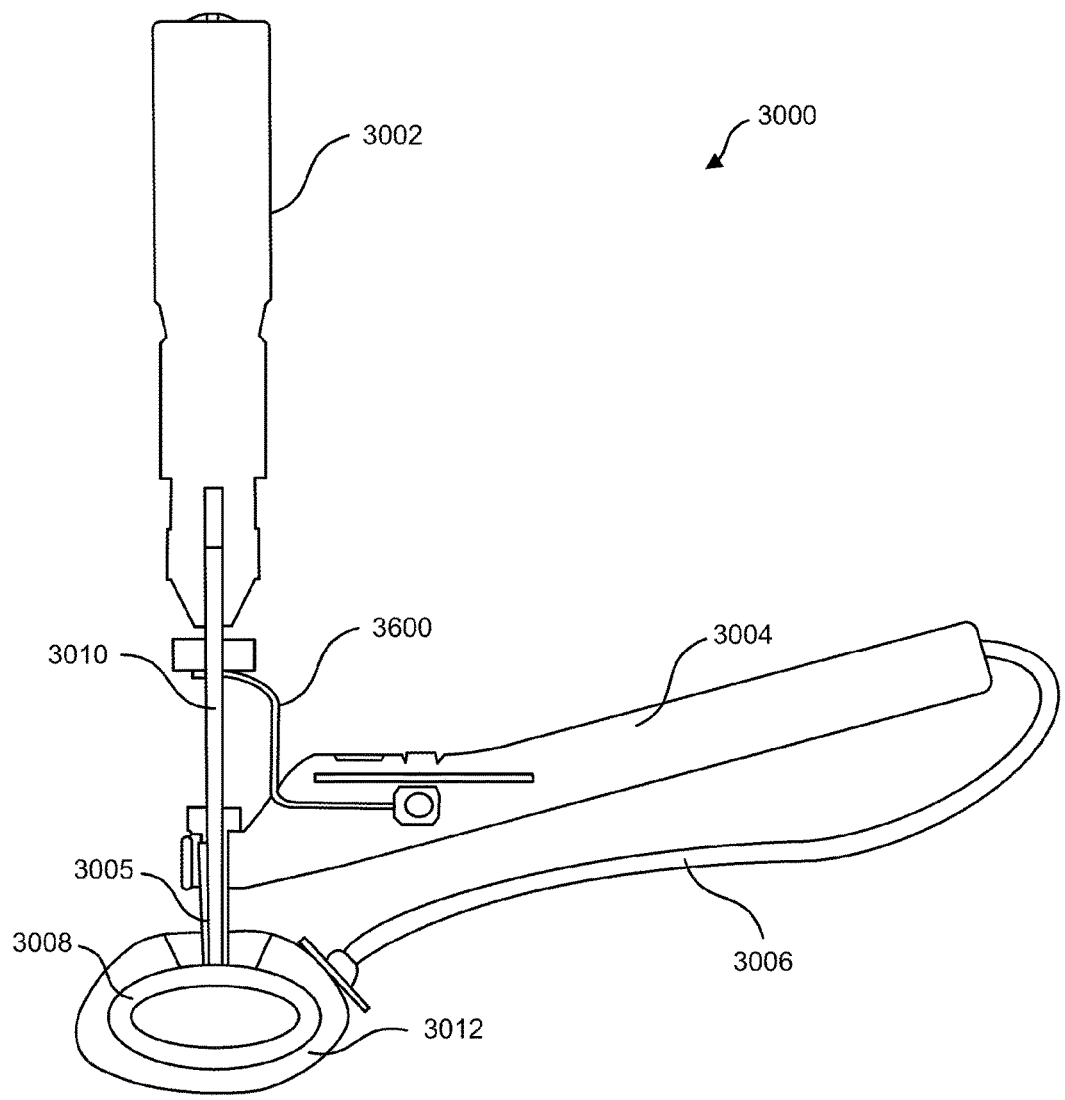
FIG. 33 shows a side section view of the drill depth measuring system of FIG. 31.
Figure 34:
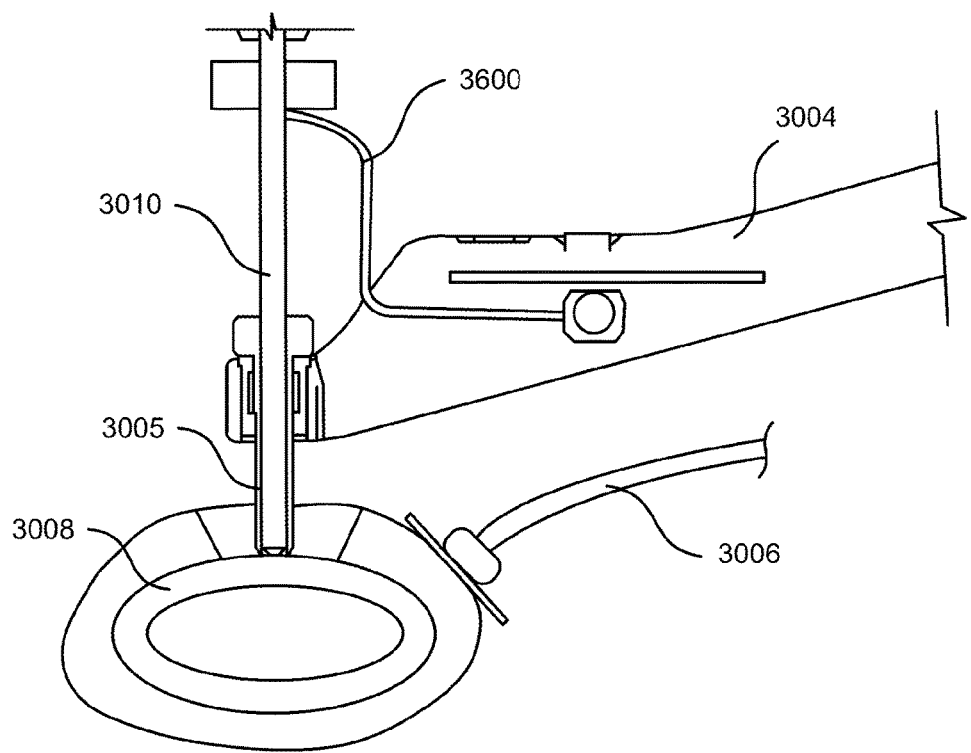
FIG. 34 shows a side-view of the drill depth measuring system of FIG. 31 showing the drill-guide engaged with the top cortical bone layer and the drill at a zeroed position.

FIGS. 32 and 33 shows the drill depth measuring system 3000 with the drill guide feature 3005 touching the bone 3008 to which the drill bit 3010 will drill into. The drill guide feature 3005 can be positioned as such prior to drilling. Alternatively or in addition, the drill bit 3010 can be advanced toward the bone 3008 until the distal end of the drill bit is in contact with a top surface of the bone 3008. Once either the drill bit 3010 or the drill guide feature 3005 are positioned this way prior to drilling, the smart drill guide 3004 (i.e., the processor determining the drill depth) can be zeroed. As such, any advancement thereafter by the drill bit 3010 can be associated with drill depth into the bone 3008. For example, FIG. 34 shows the drill depth measuring system with the distal end of the drill bit 3010 and drill guide feature 3005 engaged with a top cortical bone layer, which can be a position where the smart drill guide 3004 can be zeroed prior to drilling.

Figure 35:
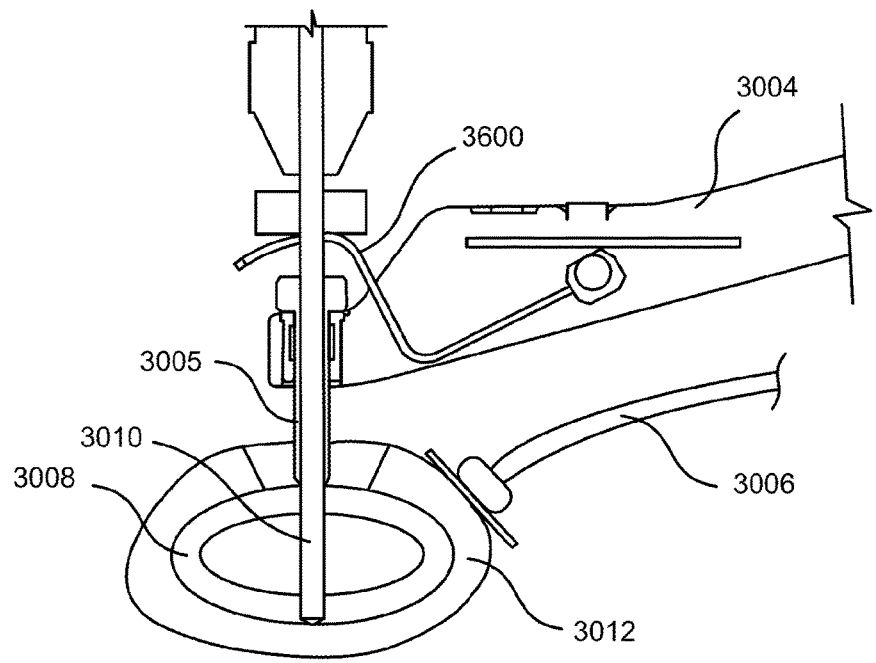
FIG. 35 shows a side-view of the drill depth measuring system of FIG. 31 with the drill through both cortical layers and contacting the bottom tissue layer.
Figure 36:
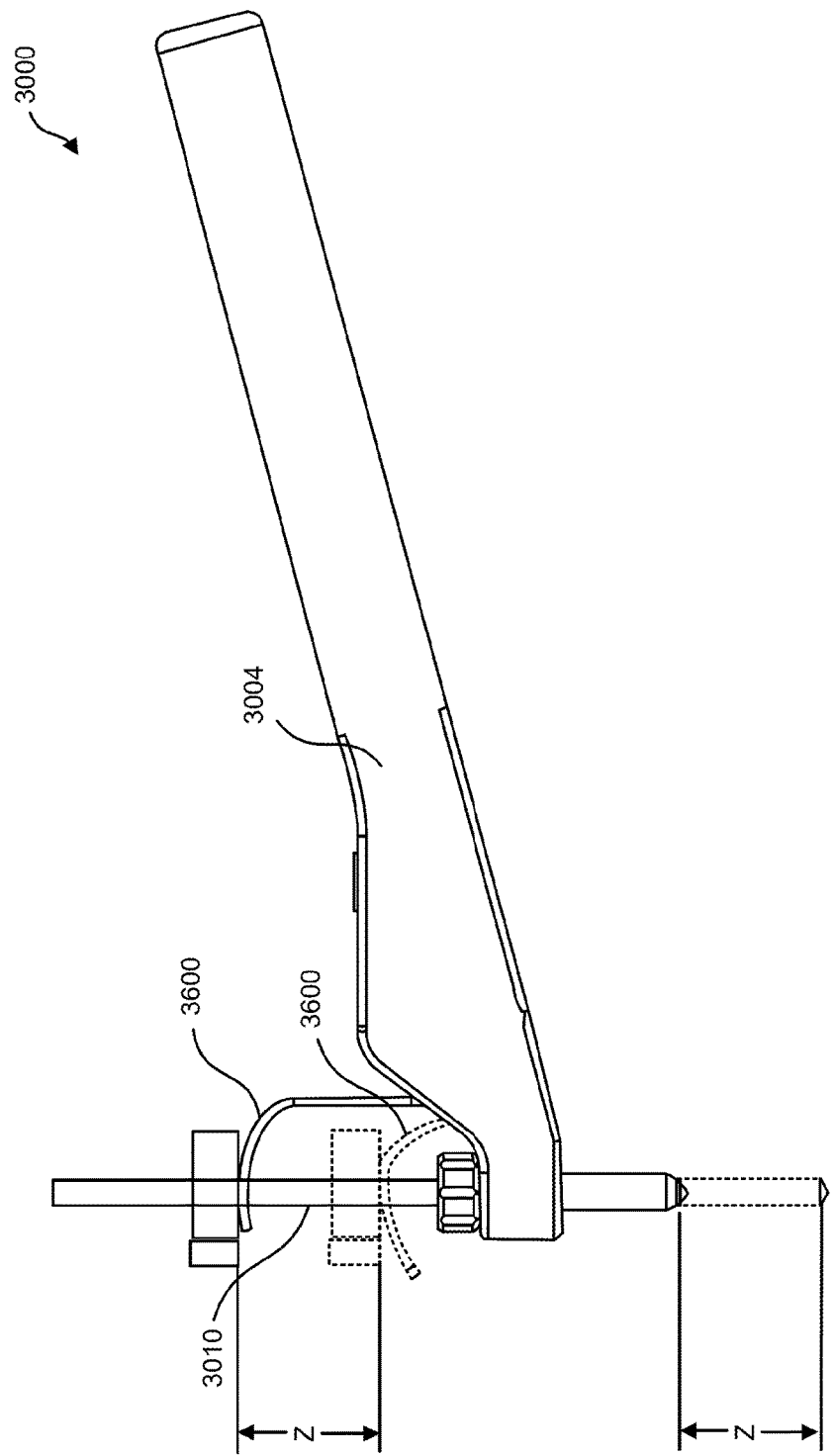
FIG. 36 shows a side view of the drill depth measuring system of FIG. 31 showing a change in z-axis positioning of the sensing lever and the drill.

FIG. 35 shows an embodiment of the drill depth measuring system 3000 with the drill bit 3010 through both cortical layers of bone 3008 and contacting a bottom tissue layer 3012. FIG. 36 shows an embodiment of the drill depth measuring system with a change in z-axis positioning of a sensing lever 3600. Such z-axis displacement can be detected by one or more sensors associated with the smart drill guide 3004, which can be used to determine a drill depth by the drill bit 3010, such as discussed above.

Figure 37:
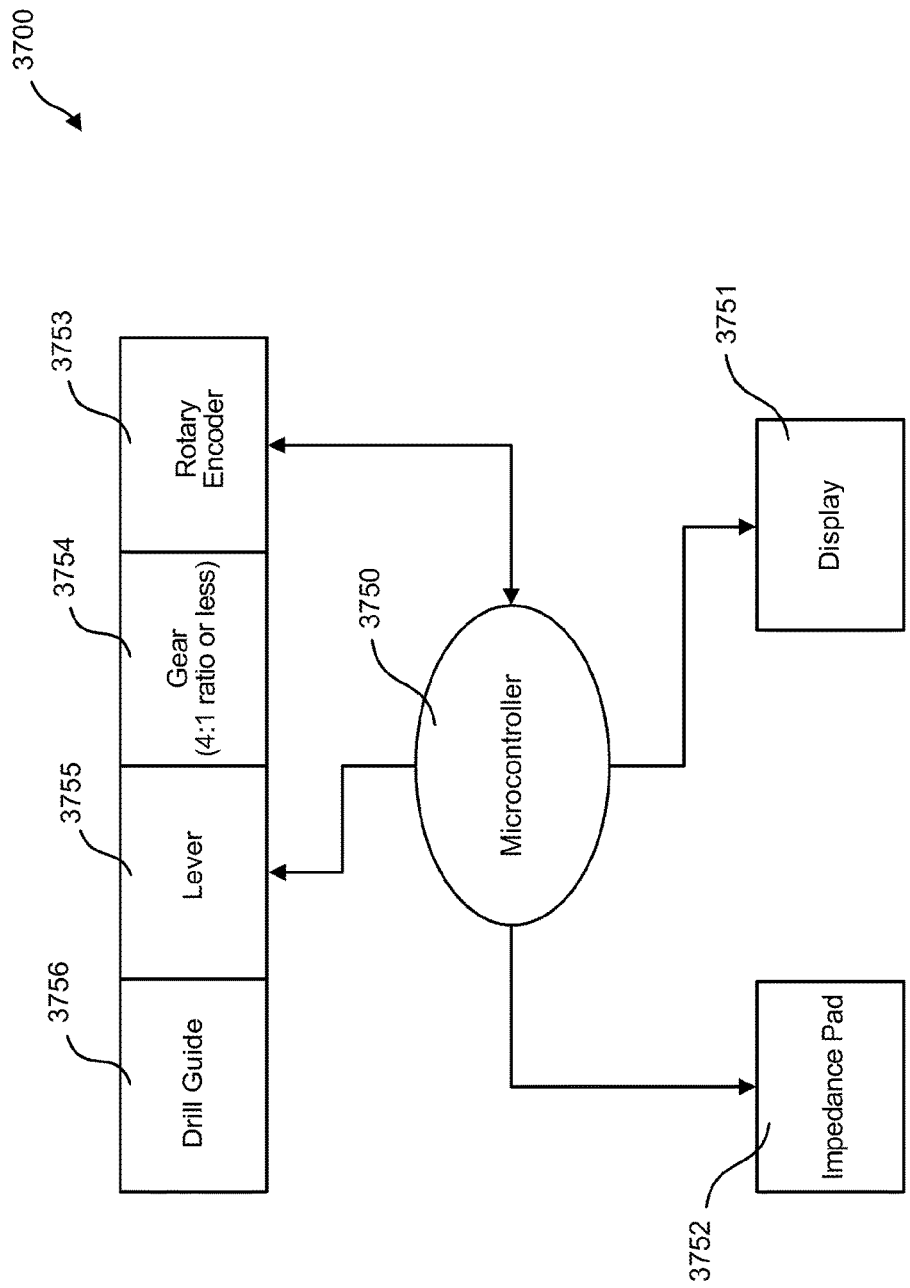
FIG. 37 illustrates an example drill depth measuring system block diagram, including communications between any one or more parts of the drill depth measuring system and a microcontroller or processor.

FIG. 37 illustrates an example drill depth measuring system block diagram 3700, including communications between any one or more parts of the drill depth measuring system and a microcontroller or processor 3750, such as a display 3751, an impedance pad 3752, a rotary encoder 3753, a gear 3754, a lever 3755, and/or a drill guide feature 3756.

Figure 38:
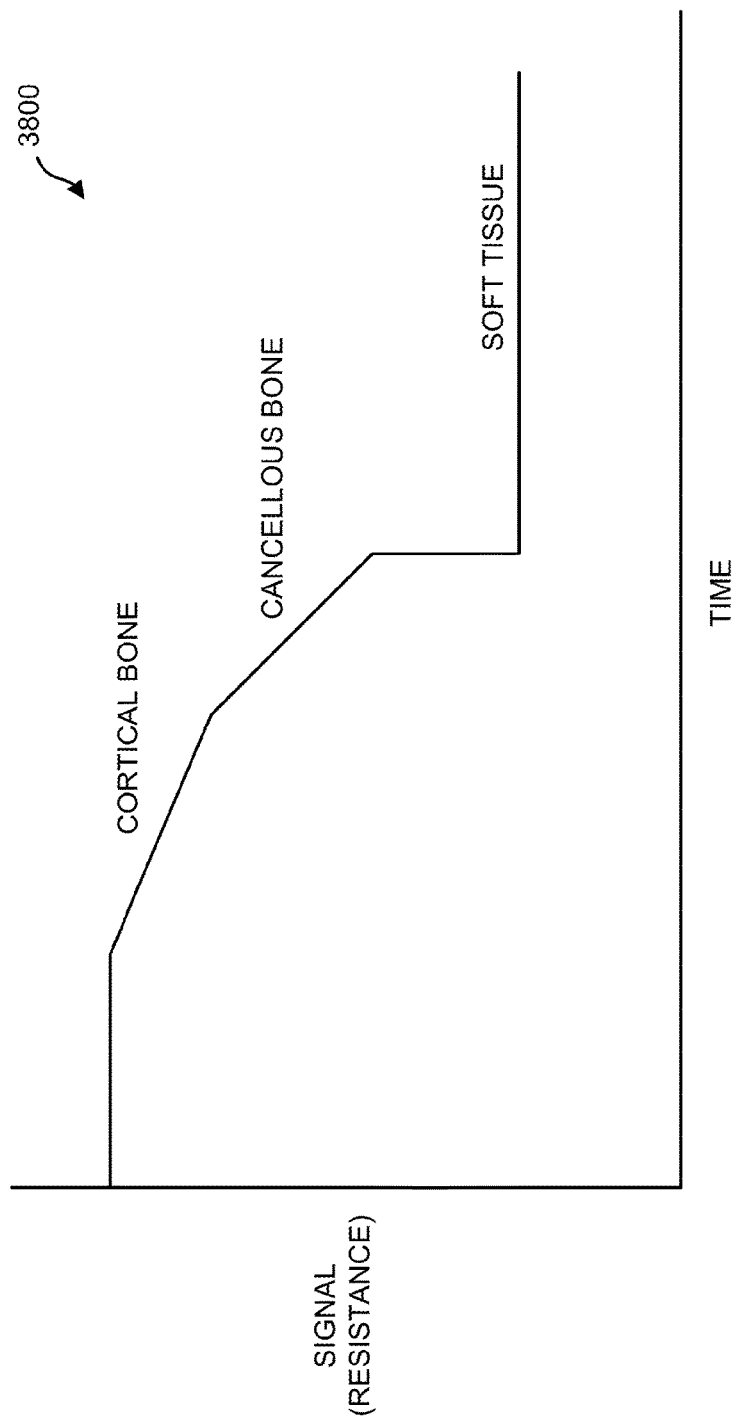
FIG. 38 illustrates an example graphical output from a resistance based system.

FIG. 38 illustrates an example graphical output 3800 from a resistance based system. For example, as shown in FIG. 38, cortical bone can provide greater resistance signals compared to cancellous bone, which can provide greater resistance signals compared to soft tissue.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. An expanding gauge device for measuring a hole formed in bone, the expanding gauge device, comprising:
   an elongated shaft having a distal surface area defined by an outer perimeter;
   a first distal pivoting element positioned adjacent the distal surface area and configured to pivot between a collapsed position and an expanded position, wherein the collapsed position includes the first distal pivoting element being positioned at least one of along and within the outer perimeter of the distal surface, and wherein the expanded position includes at least a part of the first distal pivoting element being positioned outside of the outer perimeter of the distal surface area;
   a proximal pivoting element positioned adjacent a proximal end of the elongated shaft and operatively coupled to the distal pivoting element such that pivoting of the proximal pivoting element causes the first distal pivoting element to pivot; and wherein the elongated shaft includes at least one marking along a length of the elongated shaft, wherein each of the at least one marking indicates a depth of the hole formed in the bone.

2. The expanding gauge device of claim 1, wherein the first distal pivoting element pivots along a plane parallel to the distal surface area.

3. The expanding gauge device of claim 1, wherein the distal surface area and the first distal pivoting element have a same outer profile shape.

4. The expanding gauge device of claim 1, wherein the first distal pivoting element includes a circular shape, a triangular shape, or a curved shape having a pointed first end and a rounded second end.

5. The expanding gauge device of claim 1, further comprising a second distal pivoting element that pivots between a first position where the second distal pivoting element is positioned at least one of within and along the outer perimeter of the distal surface area and a second position where at least a part of the second distal element is not within the outer perimeter of the distal surface.

6. The expanding gauge device of claim 5, wherein the first distal pivoting element is proximal to the second pivoting element.

7. The expanding gauge device of claim 5, wherein the first and second distal pivoting elements pivot along the same plane.

8. The expanding gauge device of claim 5, wherein the first and second distal pivoting elements pivot in opposite directions when pivoting into the expanded position.

9. The expanding gauge device of claim 1, wherein the first distal pivoting element includes a proximal surface configured to abut a distal surface of the bone when the elongate shaft is extending through the hole to allow a marking of the at least one marking to be positioned adjacent a proximal surface of the bone for taking a depth measurement of the hole formed in the bone.

10. A method of measuring a depth of a hole formed in bone, comprising:
    advancing a distal end of an expanding gauge through the hole formed in the bone, the expanding gauge comprising an elongated shaft having a distal surface area defined by an outer perimeter, the expanding gauge further comprising a first distal pivoting element positioned adjacent the distal surface area and configured to pivot and between a collapsed position and an expanded position, wherein the collapsed position includes the first distal pivoting element being positioned at least one of along and within the outer perimeter of the distal surface, and wherein the expanded position includes at least a part of the first distal pivoting element being positioned outside of the outer perimeter of the distal surface area;
    pivoting the first distal pivoting element from the collapsed position to the expanded position;
    abutting a proximal surface of the first distal pivoting element against a distal surface of the bone thereby allowing a marking along the elongate shaft to be positioned adjacent a proximal surface of the bone for taking a depth measurement of the hole.

* * * * *